(12) United States Patent
Nims et al.

(10) Patent No.: US 8,892,999 B2
(45) Date of Patent: Nov. 18, 2014

(54) INTERACTIVE AVATAR FOR SOCIAL NETWORK SERVICES

(75) Inventors: Jason Nims, Portland, OR (US);
Roberto Tagliabue, Lake Owego, OR (US); Danielle Quatrochi, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 880 days.

(21) Appl. No.: 12/324,140

(22) Filed: Nov. 26, 2008

(65) Prior Publication Data
US 2009/0144639 A1 Jun. 4, 2009

Related U.S. Application Data

(60) Provisional application No. 60/991,589, filed on Nov. 30, 2007.

(51) Int. Cl.
*G06F 3/048* (2013.01)
*G06F 3/00* (2006.01)
(Continued)

(52) U.S. Cl.
CPC ......... *G06N 3/006* (2013.01); *A63F 2300/8005* (2013.01); *A63B 2024/0068* (2013.01); *A63B 2220/40* (2013.01); *A63B 2071/0638* (2013.01); *A63B 24/0059* (2013.01); *A61B 5/4866* (2013.01); *G06F 17/3089* (2013.01); *A63B 2230/06* (2013.01); *G06Q 10/10* (2013.01); *A61B 5/0022* (2013.01); *A63B 2230/75* (2013.01); *A63B 69/0028* (2013.01); *A63F 2300/407* (2013.01); *A63F 2300/609* (2013.01); *A63F 2300/69* (2013.01); *A63F 2300/5553* (2013.01); *A63F 2300/572* (2013.01); *A63B 2220/20* (2013.01); *A63B 24/0075* (2013.01); *A63B 2225/50* (2013.01); *A63B 2024/0096* (2013.01); *A61B 5/744* (2013.01); *A61B 5/1118* (2013.01)
USPC .............. 715/706; 715/757; 715/760; 705/28

(58) Field of Classification Search
CPC .................. A63F 2300/5553; G06Q 30/0643; G06Q 10/087
USPC ............................ 715/757, 706; 705/27.2, 28
See application file for complete search history.

(56) References Cited

U.S. PATENT DOCUMENTS 6,817,979 B2 * 11/2004 Nihtila ........................... 600/300
7,386,799 B1 * 6/2008 Clanton et al. ................. 715/758
(Continued)

FOREIGN PATENT DOCUMENTS

JP 11-328124 11/1999
JP 2002-000941 1/2002
(Continued)

OTHER PUBLICATIONS

International Search Report and Written Opinion for application No. PCT/US2008/085138 mailed May 5, 2011.
(Continued)

*Primary Examiner* — Nicholas Ulrich
(74) *Attorney, Agent, or Firm* — Banner & Witcoff, Ltd.

(57) ABSTRACT

An embodiment is an avatar or avatar environment to visualize data within an athletic performance system or service and/or a social network system or service, for example as part of the Internet. The avatar may further evolve or alter its appearance, animation, or other visual or audio characteristics in response to the data or other input. In particular, the avatar of an embodiment may respond to and provide visualization of athletic or sport performance data. According to one or more aspects, an avatar may be placed on other network sites and updated based on athletic performance data. The avatar may be awarded for goals achieved by a user. The awards or gifts may further include non-avatar related items such as apparel, gift cards and the like.

26 Claims, 27 Drawing Sheets

(51) Int. Cl.

| | | |
|---|---|---|
| *G06Q 10/00* | (2012.01) | |
| *G06F 17/30* | (2006.01) | |
| *G06Q 10/10* | (2012.01) | |
| *G06N 3/00* | (2006.01) | |
| *A61B 5/11* | (2006.01) | |
| *A63B 24/00* | (2006.01) | |
| *A63B 71/06* | (2006.01) | |
| *A61B 5/00* | (2006.01) | |
| *A63B 69/00* | (2006.01) | |

(56) References Cited

U.S. PATENT DOCUMENTS

| | | | |
|---|---|---|---|
| 7,468,729 B1* | 12/2008 | Levinson | 345/473 |
| 8,088,002 B2* | 1/2012 | Ganz | 463/29 |
| 2003/0108851 A1 | 6/2003 | Posa | |
| 2004/0078208 A1 | 4/2004 | Burwell | |
| 2004/0131997 A1 | 7/2004 | McGuire et al. | |
| 2005/0137015 A1* | 6/2005 | Rogers et al. | 463/42 |
| 2005/0143174 A1 | 6/2005 | Goldman et al. | |
| 2006/0080613 A1 | 4/2006 | Savant | |
| 2006/0268007 A1* | 11/2006 | Gopalakrishnan | 345/619 |
| 2007/0033069 A1* | 2/2007 | Rao et al. | 705/2 |
| 2007/0113181 A1 | 5/2007 | Blattner et al. | |
| 2007/0173705 A1* | 7/2007 | Teller et al. | 600/300 |
| 2007/0197274 A1* | 8/2007 | Dugan | 463/7 |
| 2008/0077489 A1* | 3/2008 | Gilley et al. | 705/14 |
| 2008/0120558 A1* | 5/2008 | Nathan et al. | 715/764 |
| 2008/0139263 A1* | 6/2008 | He et al. | 463/6 |
| 2008/0189188 A1* | 8/2008 | Morgenstern | 705/26 |
| 2008/0244414 A1* | 10/2008 | Marcoullier et al. | 715/738 |
| 2009/0012988 A1* | 1/2009 | Brown | 707/102 |
| 2009/0048070 A1* | 2/2009 | Vincent et al. | 482/8 |
| 2009/0193343 A1* | 7/2009 | Jones et al. | 715/753 |
| 2010/0131878 A1* | 5/2010 | Fujioka | 715/765 |
| 2010/0203963 A1* | 8/2010 | Allen et al. | 463/30 |

FOREIGN PATENT DOCUMENTS

| | | |
|---|---|---|
| JP | 2003-154168 A | 5/2003 |
| JP | 2003-157240 | 5/2003 |
| JP | 2005-018212 | 1/2005 |
| JP | 2005-50611 | 3/2005 |
| JP | 2005-292498 | 10/2005 |
| JP | 2006-099448 | 4/2006 |
| JP | 2006-350416 | 12/2006 |
| WO | 2007/127642 | 11/2001 |
| WO | 02/19295 | 3/2002 |

OTHER PUBLICATIONS

International Preliminary Report on Patentability for application No. PCT/US2008/085138 mailed May 26, 2011.
Office Action received for corresponding Korean Application 10-2010-7013194, mailed Aug. 25, 2011.
First Office Action for Chinese patent application No. 2008801236739 mailed Dec. 21, 2011.
CN Office Action received Aug. 22, 2012 in corresponding U.S. Application No. 200880123673.9.
The Third Office Action of related Chinese patent application No. 200880123673.9 mailed Dec. 21, 2012.
Decision of Rejection of related Japanese patent application No. 2010-536219 mailed Feb. 4, 2013.
Canadian Office Action for application 2,706,186 mailed Apr. 3, 2013.
Text of the Rejection Decision in Chinese patent application No. 2008801236739 mailed May 31, 2013.
AU Office Action in Corresponding Australian Application No. 2008334049; dated May 11, 2012.
Notice of Reasons for Rejection for corresponding Japanese Patent Application No. 2010-536219 dated May 9, 2012.
Notice of Final Rejection for corresponding Korean Patent Application No. 10-2010-7013194 dated Apr. 30, 2012.
Apr. 15, 2014 Office Action issued in Canadian Patent Application No. 2,706,186.
Feb. 4, 2014 Office Action issued in Korean Patent Application No. 10-2012-7022952.
Notice of Reasons for Rejection for Japanese Patent Application No. 2013-115245 dated Jun. 23, 2014.
Notice of Final Rejection dated Aug. 22, 2014, issued in corresponding Korean Patent Application No. 10-2012-7022952.
Notice of Reasons for Rejection dated Aug. 28, 2014, issued in corresponding Japanese Patent Application No. 2010-536219.

\* cited by examiner

| Home | Profile | Friends | Inbox | | Settings | Logout | Search |

Avatar

MY AVATAR

My Avatar isn't feeling social. Try back some other time.

Your avatar widget requires a Screen Name to get going. Simply grab it from xyz.com and paste or type it below.

Don't have an avatar? Create one now ▸  1505

Screen Name (case-sensitive)

| ScreennameOne | SUBMIT |  1503

1507 { Hey, this profile is private. Set it to public on xyz.com to see your Avatar.
Sorry we could not find the member name.

1500

Check out your profile ▸
Remove Avatar from your profile ▸

FIG. 15

INTERACTIVE AVATAR FOR SOCIAL NETWORK SERVICES

CROSS REFERENCE TO RELATED APPLICATIONS

The present application is a continuation-in-part of and claims the benefit of and priority to U.S. Patent Application No. 60/991,589, filed Nov. 30, 2007, which application is incorporated by reference and made a part hereof.

BACKGROUND

A social network system or service focuses on the building and verifying of online social networks for communities of people who share interests and activities, or who are interested in exploring the interests and activities of others, and which necessitates the use of software. Most social network services are primarily web based and provide a collection of various ways for users to interact, such as chat, messaging, email, video, voice chat, file sharing, blogging, discussion groups, and so on. The main types of social networking services are those which contain directories of some categories (such as former classmates), means to connect with friends (usually with self-description pages), and recommender systems linked to trust. For example, and among myriad interests, a social networking service, or application thereof, may focus on athletes and athletics, members of which may interact regarding their athletic interests and activities. Social networking services may further include or describe a framework for application development. Such applications may interact with core social networking service functionality or other applications to customize the social networking service. For example, a social networking service user may include one or more applications to customize or extend the functionality of the social networking service.

Within the social network service, a user may be represented by an avatar. Generally speaking, an avatar may be a graphical two-dimensional icon or a 3-dimensional model that may represent a user. An avatar may be as simple as a picture of the user or may be a graphical object that may represent the user's actions, beliefs, interests, appearance, identity, personality, and the like. An avatar may be further animated. In addition to representing the characteristics recited above, a user may opt to utilize an avatar—particularly a graphical icon or model—to maintain their anonymity while participating in and interacting with the social network service.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

One or more aspects relate to the use of avatars to digitally represent a user and his or her athletic performance. In one configuration, the avatar may be awarded prizes that alter the avatar's appearance upon a user completing an athletic performance goal. For example, upon a user completing a first workout, a new shirt or pair of shoes may be unlocked for the avatar. The avatar may then be updated with the new shirt or pair of shoes. Thus, an avatar may be provided with an object based on a predetermined occurrence. Awards or gifts may further include real-life objects for the athlete such as gift cards, apparel, coupons and the like.

According to another aspect, avatar awards may be used to motivate users to complete goals and fulfill their resolutions. In one example, a user may set a goal or resolution for the upcoming year. To keep the user on track and motivated, awards for the user and/or avatar may be given along the way. The goal may, in some instances, be divided into sub-goals for which awards may be provided upon completion.

According to another aspect, avatars may be placed on other network sites (e.g., webpages) using an avatar widget. An avatar widget may automatically receive or retrieve athletic performance and avatar data associated with the user and update the widget. Thus, if a user's avatar is given new clothes on a first website, the avatar's widget on a second website may be automatically updated. Athletic performance information of the user may also be updated in similar fashion.

According to another aspect, awards, prizes and other items may be gifted from one user to another. For example, a first user may receive an avatar item by purchase or as an award and decide to gift it to a second user in recognition of some accomplishment of the second user.

Avatars may further be downloaded as a screensaver that provides avatar information as well as athletic performance information.

BRIEF DESCRIPTION OF THE DRAWINGS

Certain embodiments are illustrated by way of example and not limited in the accompanying figures in which like reference numerals indicate similar elements and in which:

FIG. 15 illustrates an example avatar widget adding interface according to one or more aspects described herein;

DETAILED DESCRIPTION

Figure 1:
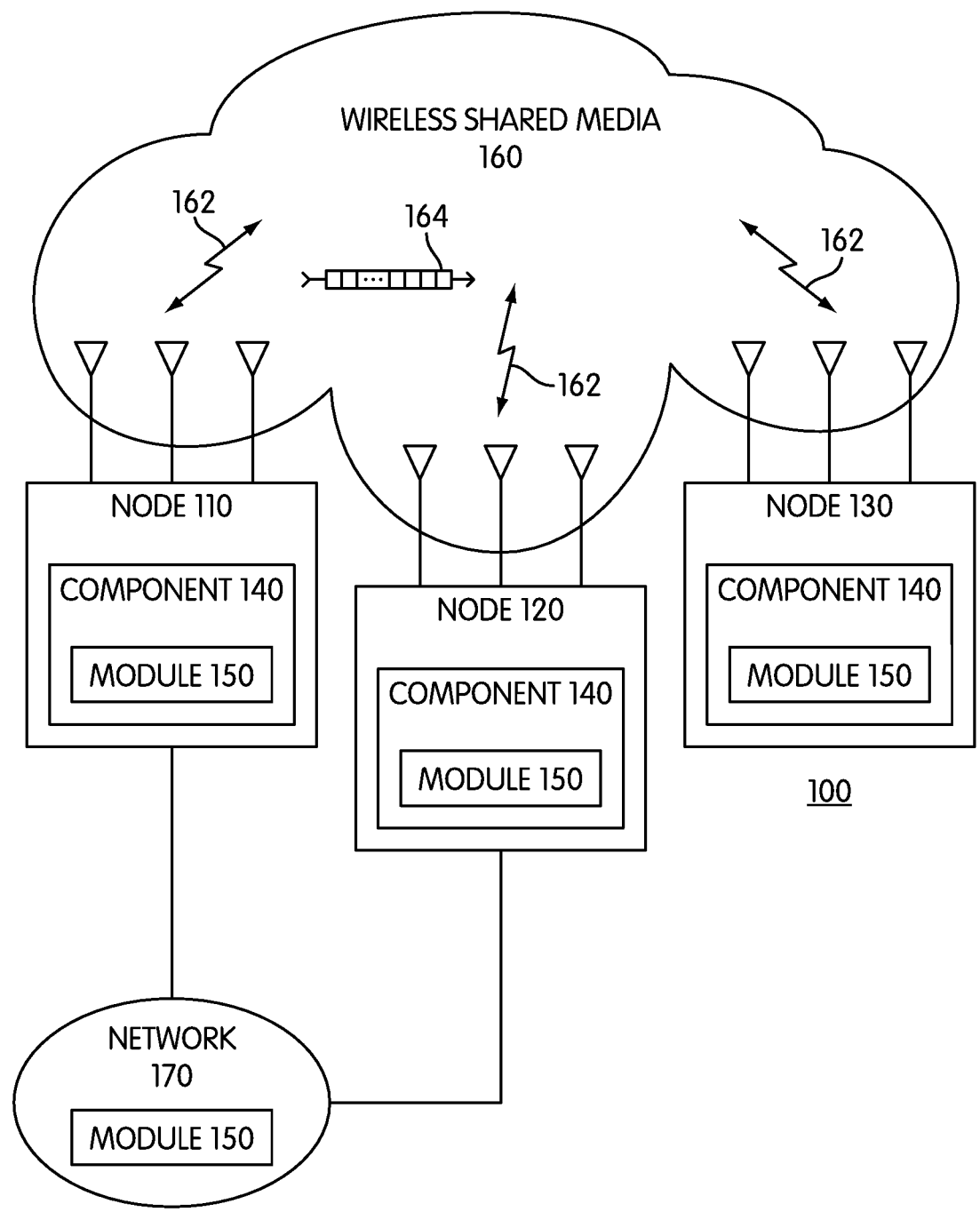
FIG. 1 illustrates a system of an embodiment according to one or more aspects described herein.

Embodiments of an interactive avatar for a social network service will be described. Reference will now be made in detail to a description of these embodiments as illustrated in the drawings. While the embodiments will be described in connection with these drawings, there is no intent to limit them to drawings disclosed herein. On the contrary, the intent is to cover all alternatives, modifications, and equivalents within the spirit and scope of the described embodiments as described herein.

An avatar or avatar environment, as used herein, may be used to visualize data within a social network system or service, for example as part of the Internet. The avatar may further evolve or alter its appearance, animation, or other visual or audio characteristics in response to the data or other input. In particular, the avatar of an embodiment may respond to and provide visualization of athletic or sport performance data.

FIG. 1 illustrates an embodiment of a system 100 in which an avatar or avatar environment may be used. In an embodiment, system 100 is a social network system comprising multiple nodes. A node generally may comprise any physical or logical entity for communicating information in the system 100 and may include hardware, firmware, software, or any combination thereof, as desired for a given set of design parameters or performance constraints. Although FIG. 1 may show a limited number of nodes by way of example, more or less nodes may be employed as desired.

In various embodiments, a node may comprise, or be implemented as, a computer system, a computer sub-system, a computer, an appliance, a workstation, a terminal, a server, a personal computer (PC), a laptop, an ultra-laptop, a hand-held computer, a personal digital assistant (PDA), a set top box (STB), a telephone, a mobile telephone, a cellular telephone, a handset, a wireless access point, a base station (BS), a subscriber station (13), a mobile subscriber center (MSC), a radio network controller (RNC), a microprocessor, an integrated circuit such as an application specific integrated circuit (ASIC), a programmable logic device (PLD), a processor such as general purpose processor, a digital signal processor (DSP) and/or a network processor, an interface, an input/output (I/O) device (e.g., keyboard, mouse, display, printer), a router, a hub, a gateway, a bridge, a switch, a circuit, a logic gate, a register, a semiconductor device, a chip, a transistor, or any other device, machine, tool, equipment, component, or combination thereof. The embodiments are not limited in this context.

In various embodiments, a node may comprise, or be implemented as, software, a software module, an application, a program, a subroutine, an instruction set, computing code, words, values, symbols or combination thereof. A node may be implemented according to a predefined computer language, manner or syntax, for instructing a processor to perform a certain function. Examples of a computer language may include C, C++, Java, BASIC, Perl, Matlab, Pascal, Visual BASIC, assembly language, machine code, microcode for a network processor, and so forth. The embodiments are not limited in this context.

The nodes of the system 100 may be arranged to communicate one or more types of information, such as media information and control information. Media information generally may refer to any data representing content meant for a user, such as image information, video information, graphical information, audio information, voice information, textual information, numerical information, alphanumeric symbols, character symbols, and so forth. Control information generally may refer to any data representing commands, instructions or control words meant for an automated system. For example, control information may be used to route media information through a system, or instruct a node to process the media information in a certain manner. The media and control information may be communicated from and to a number of different devices or networks.

The system 100 may include one or more nodes (e.g., nodes 110-130) arranged to communicate information over one or more wired and/or wireless communications media. Examples of wired communications media may include a wire, cable, printed circuit board (PCB), backplane, switch fabric, semiconductor material, twisted-pair wire, co-axial cable, fiber optics, and so forth. An example of a wireless communication media may include portions of a wireless spectrum, such as the radio-frequency (RF) spectrum. In such implementations, the nodes of the system 100 may include components and interfaces suitable for communicating information signals over the designated wireless spectrum, such as one or more transmitters, receivers, transceivers, amplifiers, filters, control logic, antennas and so forth.

The communications media may be connected to a node using an input/output (I/O) adapter. The I/O adapter may be arranged to operate with any suitable technique for controlling information signals between nodes using a desired set of communications protocols, services or operating procedures. The I/O adapter may also include the appropriate physical connectors to connect the I/O adapter with a corresponding communications medium. Examples of an I/O adapter may include a network interface, a network interface card (NIC), a line card, a disc controller, video controller, audio controller, and so forth.

In various embodiments, the communications system 100 may comprise or form part of a network (e.g., network 170), such as a WiMAX network, a broadband wireless access (BWA) network, a WLAN, a WMAN, a wireless wide area network (6AN), a wireless personal area network (WPAN), a Code Division Multiple Access (CDMA) network, a Wideband CDMA (WCDMA) network, a Time Division Synchronous CDMA (TD-SCDMA) network, a Time Division Multiple Access (TDMA) network, an Extended-TDMA (E-TDMA) network, a Global System for Mobile Communications (GSM) network, an Orthogonal Frequency Division Multiplexing (OFDM) network, an Orthogonal Frequency Division Multiple Access (OFDMA) network, a North American Digital Cellular (NADC) network, a Universal Mobile Telephone System (UMTS) network, a third generation (3G) network, a fourth generation (4G) network, a local area network (LAN), a wide area network (WAN), a metropolitan area network (MAN), the Internet, the World Wide Web, a cellular network, a radio network, a satellite network, and/or any other communications network configured to carry data. The embodiments are not limited in this context.

In an embodiment, system 100 may include node 130. Node 130 may comprise, for example, a mobile device or a fixed device having wireless capabilities. A mobile device may comprise a generalized equipment set providing connectivity to other wireless devices, such as other mobile devices or fixed devices. Examples for node 130 may include a computer, server, workstation, notebook computer, handheld computer, telephone, cellular telephone, personal digital assistant (PDA), combination cellular telephone and PDA, and so forth.

Nodes 110-130 may have one or more wireless transceivers and wireless antennas. In one embodiment, for example, nodes 110-130 may each have multiple transceivers and multiple antennas to communicate information signals over wireless shared media 160. For example, a channel 162, link, or connection may be formed using one or more frequency bands of wireless shared medium 160 for transmitting and receiving packets 164. The embodiments are not limited in this context.

Figure 2:
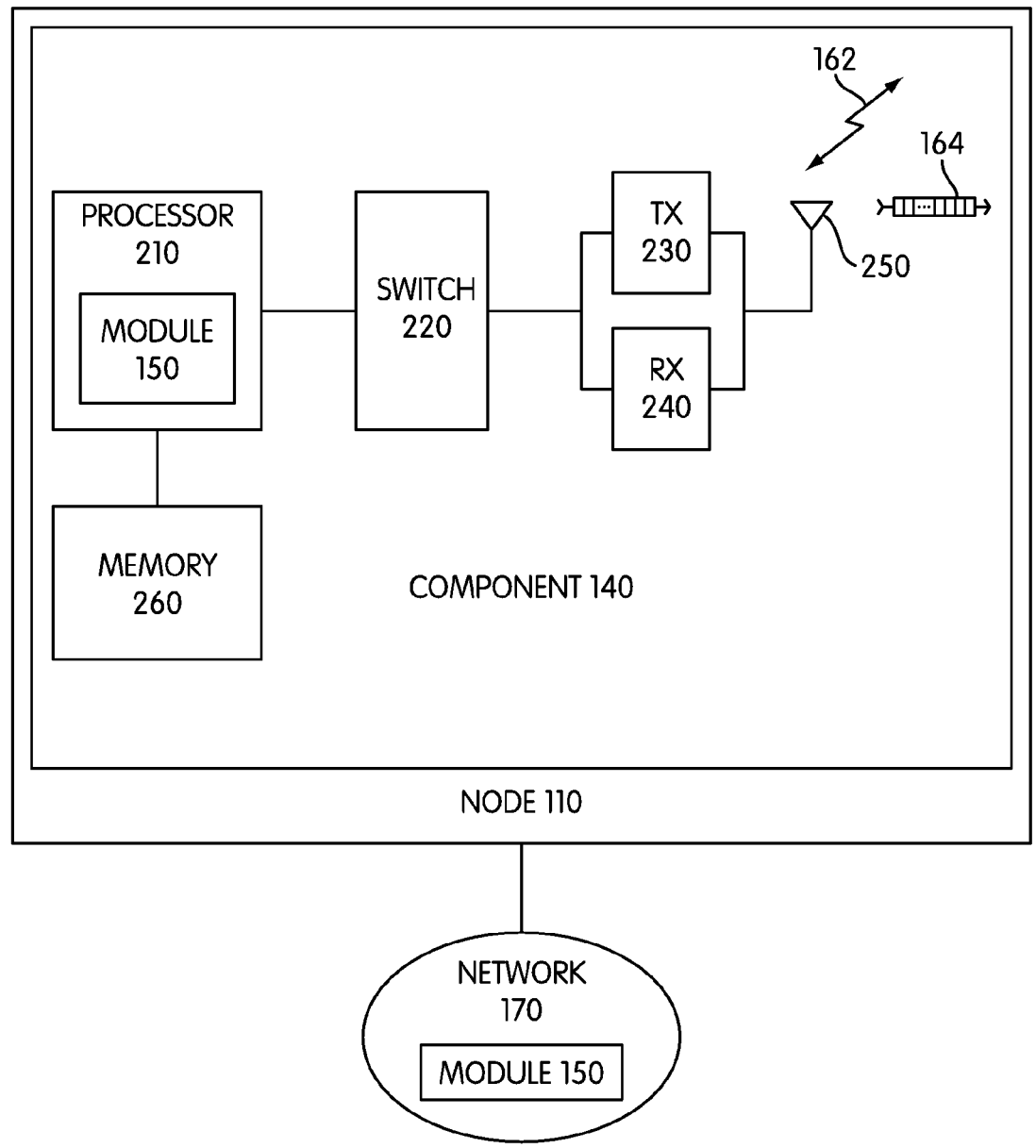
FIG. 2 illustrates a social network service node of an embodiment according to one or more aspects described herein.

FIG. 2 more specifically illustrates node 110 of the communications system 100. As shown in FIG. 2, the node may comprise multiple elements such as component 140, module 150, processor 210, memory 260, switch 220, transmitter 230, receiver 240, and antenna 250 to communicate packets 164 over wireless shared media 160. Transmitter 230 and receiver 240 may also be collectively referred to as a transceiver. Some elements may be implemented using, for example, one or more circuits, components, registers, processors, software subroutines, or any combination thereof. Although FIG. 2 shows a limited number of elements, it can be appreciated that additional or fewer elements may be used in node 110 as desired for a given implementation. The embodiments are not limited in this context.

As noted, in an embodiment, node 110 may include a processor 210. Processor 210 may be connected to switch 220 and/or the transceiver (i.e., transmitter 230 and receiver 240). Processor 210 may be implemented using any processor or logic device, such as a complex instruction set computer (CISC) microprocessor, a reduced instruction set computing (RISC) microprocessor, a very long instruction word (VLIW) microprocessor, a processor implementing a combination of instruction sets, or other processor device. In an embodiment, for example, processor 210 may be implemented as a general purpose processor. Processor 210 may also be implemented as a dedicated processor, such as a controller, microcontroller, embedded processor, a digital signal processor (DSP), a network processor, a media processor, an input/output (I/O) processor, a media access control (MAC) processor, a radio baseband processor, a field programmable gate array (FPGA), a programmable logic device (PLD), and so forth. The embodiments are not limited in this context.

In one embodiment, processor 210 may include, or have access to, memory 260. Memory 260 may comprise any machine-readable media. Memory 260 may be implemented using any machine-readable or computer-readable media capable of storing data, including both volatile and non-volatile memory. For example, memory 260 may include read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, or any other type of media suitable for storing information. It is worthy to note that some portion or all of memory 260 may be included on the same integrated circuit as processor 210, or alternatively some portion or all of memory 260 may be disposed on an integrated circuit or other medium, for example a hard disk drive, that is external to the integrated circuit of processor 210. The embodiments are not limited in this context.

When implemented in a node of system 100, node 110 may be arranged to communicate information over wired or wireless communications media between the various nodes, such as nodes 120 and 130. The information may be communicated using in the form of packets 164 over wireless shared media 160, with each packet 164 comprising media information and/or control information. A packet 164 in this context may refer to any discrete set of information, including a unit, frame, cell, segment, fragment, and so forth. The packet may be of any size suitable for a given implementation. The embodiments are not limited in this context.

In an embodiment for which system 100 is a social network system, module 150 may include an avatar module. As introduced, an avatar may be any representation or manifestation including but not limited to a static or animated picture of a user, or the avatar may be a graphical object that may represent the user's actions, beliefs, interests, appearance, identity, personality, and the like when the user participates in and interacts with a social network. The avatar module of an embodiment may allow a user to select a pre-designed avatar representative of themselves for use in the social network system or service. The user may further customize or otherwise alter the pre-designed avatar (e.g., color scheme and the like) to generate a more desirable representation of themselves. The avatar module of an alternate embodiment may allow the user to upload or otherwise create an avatar of substantially or entirely custom design.

Figure 3:
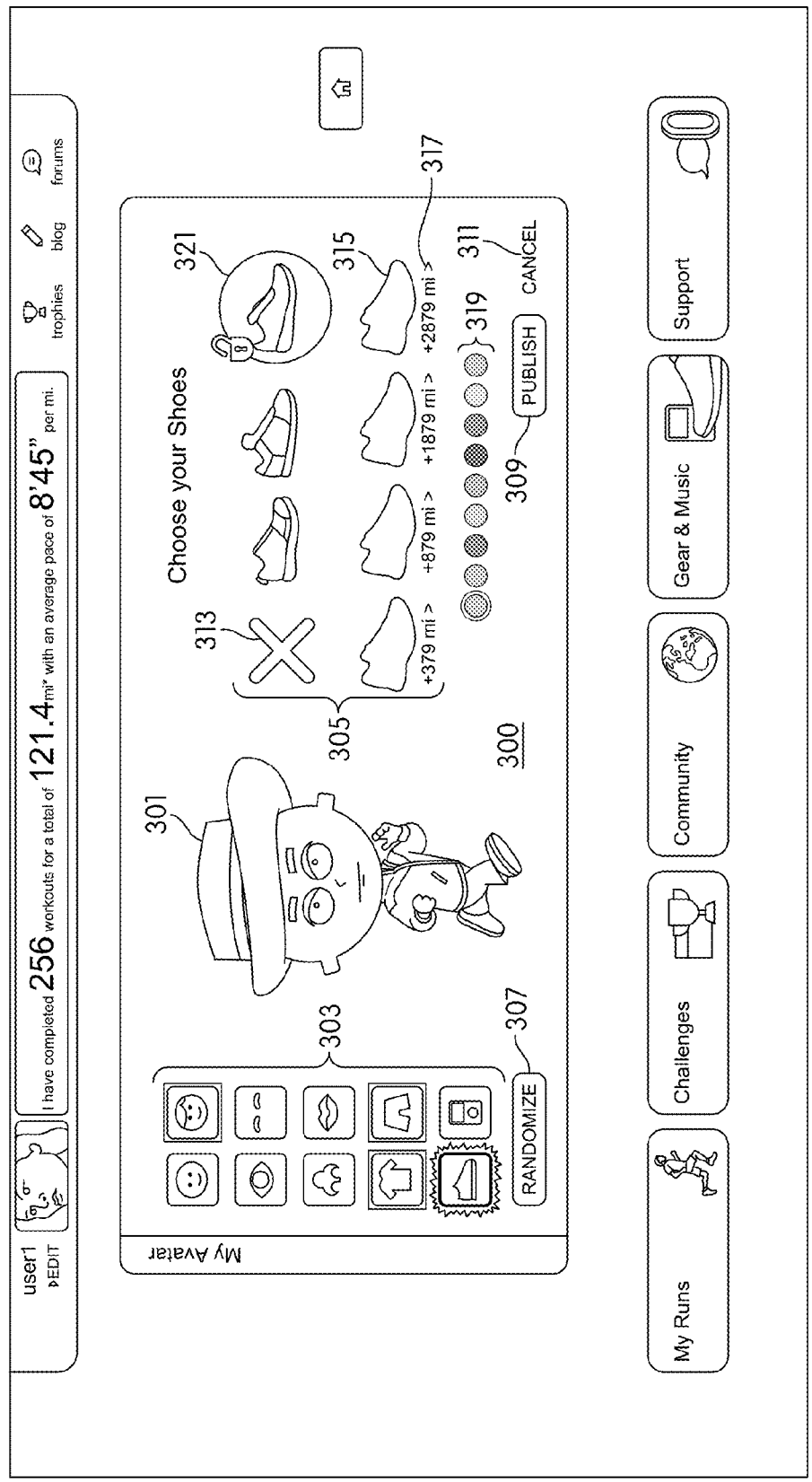
FIGS. 3 and 4 illustrate example avatar creation and customization interfaces according to one or more aspects described herein.

FIG. 3 illustrates an example avatar creation and customization interface through which a user may create a new avatar. Avatar creation interface 300 may initially display a default avatar 301, feature categories 303, specific features 305, a randomize option 307, a publish option 309 and a cancel option 311. Starting from default avatar 301, a user may modify various characteristics such as hair style or color, facial expression, lips, eye brows, eyes, nose, shirt, pants, shoes and accessories. Although not illustrated, other characteristics may also be modifiable. For example, in some embodiments, an avatar's body shape, ears and hands may be customized. Using categories 303, each of the above mentioned characteristics may be customized according to the user's preference. In one example, and as illustrated, a user may modify the shoes that avatar 301 is wearing. In particular, specific features 305 include a variety of shoes that are available to the user for his or her avatar. In some instances, new shoes or other features might only be available upon completion of a certain challenge, action, goal or the like. The shoes available for the avatar could also correspond to a latest actual shoe model offered by a shoe manufacturer or some other shoe design currently in fashion among users. The unavailable shoes 315 or other feature might be shown in a dark outline (i.e., without significant details) along with the goal 317 that needs be met. For example, some shoes might not be available for selection until a user has run a specified distance. A user may further select the 'X' option 313 if he or she wishes to remove shoes from avatar 301. Additionally, a user may select a color of the shoe or other feature being customized using color palette 319. An unlocked lock symbol 321 next to or otherwise associated with a selectable feature may indicate that the selectable feature is newly available to the user.

Figure 4:
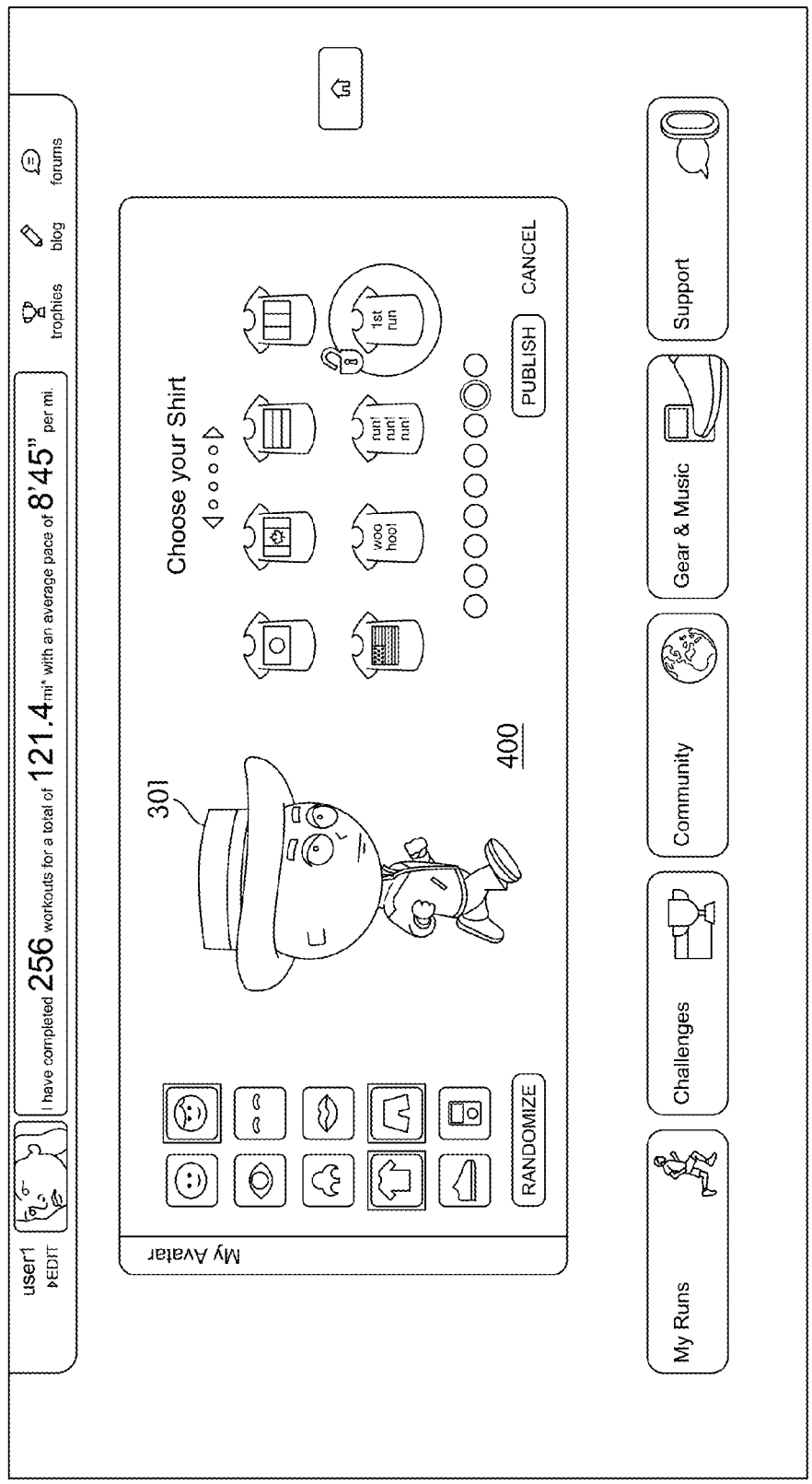
Figure 5:
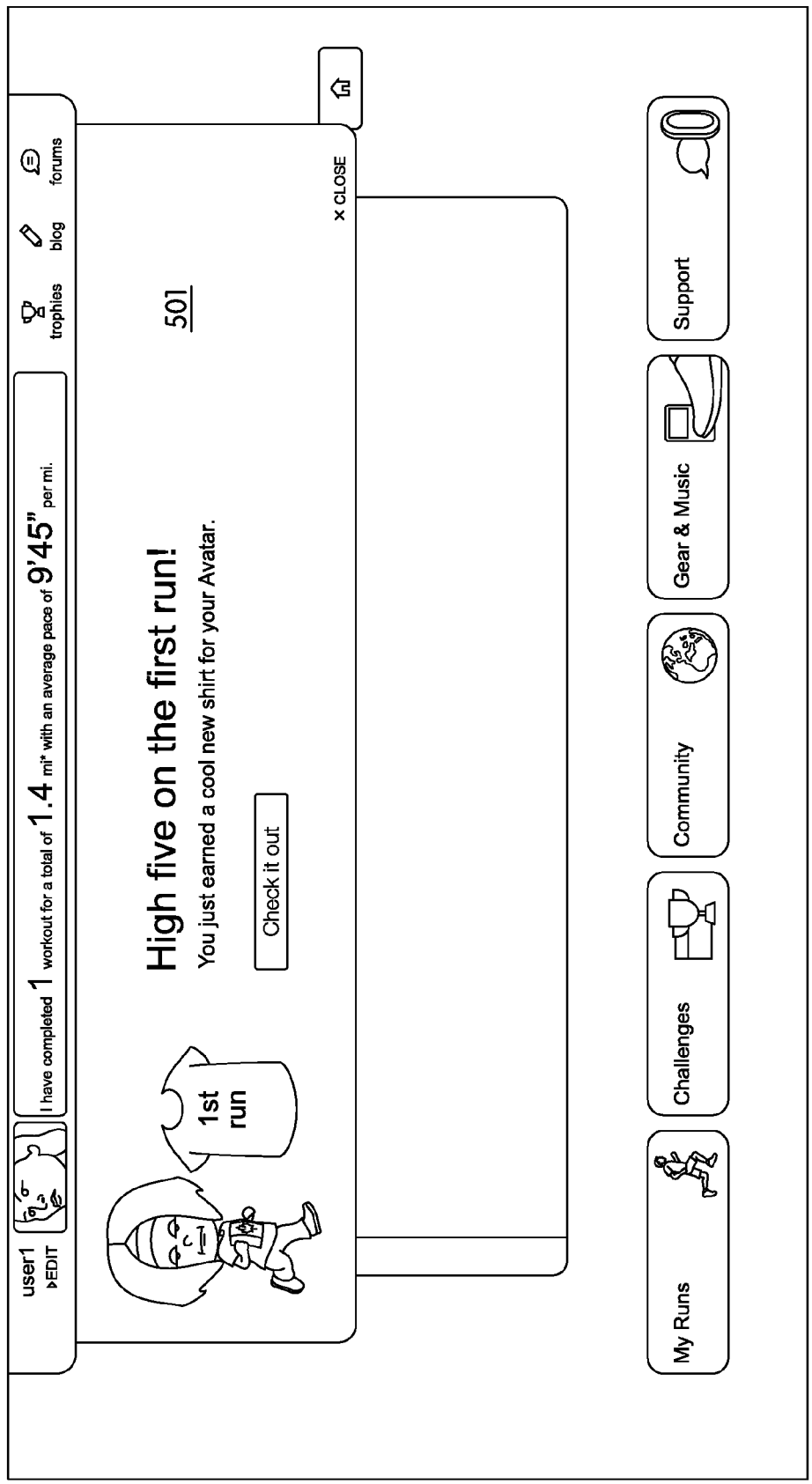
FIGS. 5-7 illustrate example notification windows according to one or more aspects described herein.

FIG. 4 illustrates another example avatar customization interface 400 where a user is able to select different shirts for avatar 301. In some instances, when a new item or selectable feature has been unlocked, a notification may be displayed to the user. For example, FIG. 5 illustrates notification window 501 being displayed upon the user earning a new shirt for the user's first run. Awards may be given for reaching certain goals such as a user's first workout. The notification window 501 may overlay the remaining interface including an avatar creation interface and an athletic performance site or interface. In one or more configurations, notification window 501 may automatically activate avatar creation/customization interface (e.g., interface 300) so that a user may immediately activate the newly available feature. Notification window 501 may be window that is part of the underlying interface or, alternatively, may be a separate interface window from the window including the underlying interface. It is understood that the above features can be utilized for any of a variety of different accessories for the avatar.

Alternatively or additionally, awards or gifts for accomplishments or achievements may include non-avatar related items such as gift cards, downloadable content such as music or videos, coupons, apparel such as t-shirts and shoes and the like. Further, awards or gifts, whether avatar related or not, may represent the most recent or most popular product. For example, an avatar may be awarded a pair of shoes that are the latest model in a line of shoe types offered by a shoe manufacturer. The ability to obtain the latest product or form of a product (such as a shoe design) may provide a further incentive for a user to continue reaching milestones and achieving goals.

Figure 6:
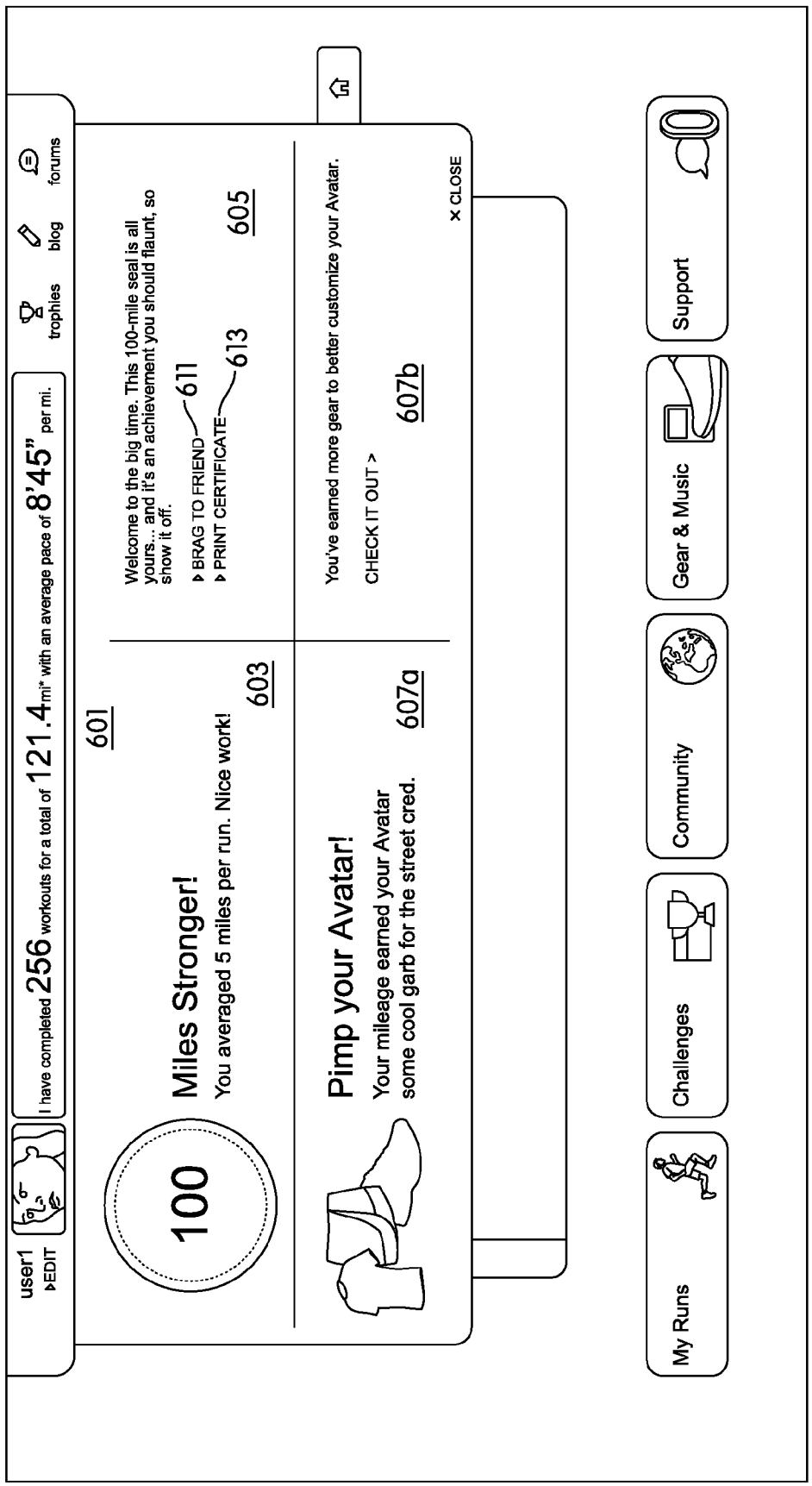

In an alternate or additional embodiment, a notification window may include other information that might not be related to the avatar. For example, FIG. 6 includes a notification window 601 that indicates the milestone achieved 603 and may also include a specialized seal, non-avatar related options 605 and avatar related options 607. Non-avatar related option 605 may include features such as bragging (i.e., sending a message) to a friend or other user 611 and printing a certificate indicating the accomplishment 613. Other non-avatar related options may include receiving/accepting a coupon (e.g., for clothing or sports related items) for reaching the milestone and issuing a challenge to another user to achieve the same milestone.

Figure 7:
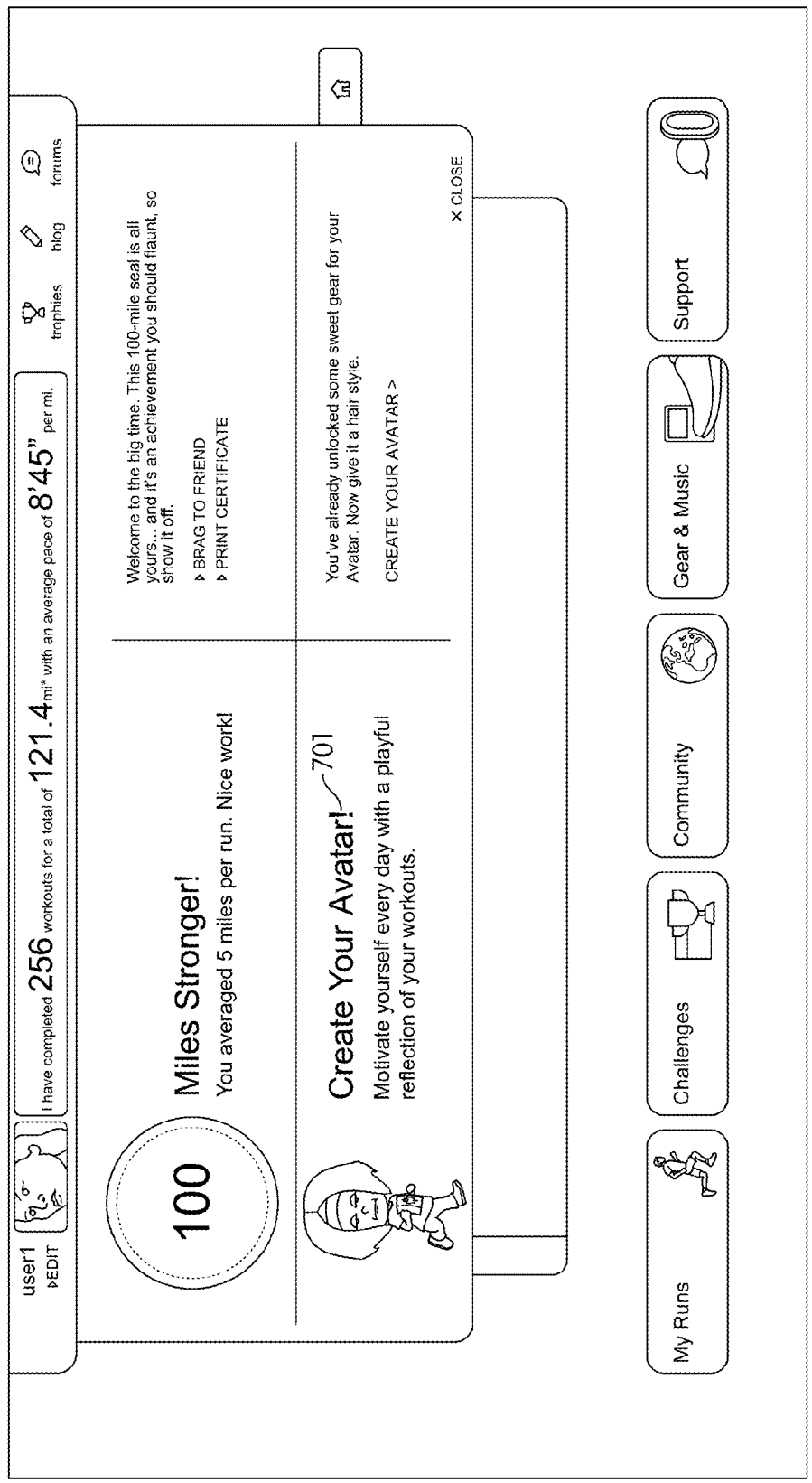

According to one or more aspects, if a user has created an avatar, notification window 601 may display avatar related options 607 such as customize your avatar 607a. However, if the user has not created an avatar, notification window 601 may instead display an invitation or option to create an avatar. Such an option 701 is illustrated in FIG. 7. Thus, even without having an avatar created, a user may still accumulate awards and/or points based on various achievements.

Referring back to FIG. 3, once the user has completed editing or creating the avatar, the user may subsequently choose to publish 309 the avatar to a website, application or other interface. Publishing the avatar may include activating the avatar for use and display in one or more interfaces. Alternatively, if a user decides that he or she does not like the changes made to the avatar 301, he or she may choose cancel option 311 to return to a previous screen or interface without making changes to a current avatar or without creating an avatar. Instead, a current or default avatar (e.g., default avatar 301 without any customization) may be used. According to one or more embodiments, a user may upload an avatar instead of creating one from a pre-specified default. For example, a user may store an avatar as an image file and upload the avatar for use in various interfaces.

In one or more configurations, avatar creation interface 300 may be included as part of a user's personal athletic performance website or application interface that includes a variety of other options such as viewing challenges, accessing community information, viewing athletic performance information and the like. Accordingly, available customization features may be unlocked based on the athletic performance information recorded by the underlying website or application interface. Features or items for an avatar may be unlocked for other accomplishments such as finishing a challenge, accepting or joining a challenge, winning a challenge, reaching a goal, coordinating activities with other users and the like. In one example, a user may be awarded with an item for completing the user's first workout.

Alternatively or additionally, a user may earn points, or some other currency, with which he or she may purchase new selectable features or options for his or her avatar rather than earning the actual feature or option. For example, a first avatar t-shirt may be purchasable for 2,000 points while a second avatar t-shirt may be purchased for 3,000 points. Instead of automatically awarding a user with the first avatar t-shirt once the user has reached 2,000 points, the user may be allowed to choose whether to purchase the first avatar t-shirt or to continue accumulating points to purchase the second avatar t-shirt. Points may be earned in similar fashion to earning selectable features. That is, points may be earned by achieving goals, joining a challenge, finishing a challenge, winning a competition, starting a challenge, inviting a friend to join a challenge or the athletic performance website and the like.

According to another aspect, a user may receive gifts or awards from another user. In one example, a first user or athlete may create a challenge and invite a second user to participate. The first user may entice others to join or otherwise take part in the challenge by offering an award of gift for winning, reaching some goal or even for just participating. Thus, upon joining, winning, reaching the specified goal or other specified condition, the gift or award may be given to the participants of the challenge. In another example, a first user may wish to provide a gift to another user in recognition of an accomplishment or goal. The gift may be purchased by the first user or may be a gift that was received for completing a goal himself or herself (e.g., an avatar shoe unlocked for running a specified distance may be transferred/gifted by the runner to another user).

Once the user has selected or generated a suitable avatar, the user may participate with and interact with a social network system or service. The avatar may represent the user in a myriad of ways depending on the configuration or purpose of the social network system or service. For example, in an embodiment, the social network system or service may allow the user to send a message to or post a comment for another user. The message or comment may be accompanied by the avatar of the sender, and may or may not represent the identity of the sender. The avatar may further represent the user in a web log (i.e., blog) or other similar self comment. Further still, the avatar may represent the athletic performance or abilities of the user, or a comparison of the athletic performance or abilities to other user(s) or benchmark(s). For example, referring again to FIG. 3, avatar 301 may be used to represent the athletic performance goals achieved by or athletic abilities of a user.

In one arrangement, a social network system or service may contain an application, plug-in, or the like to track, monitor, and/or visually display athletic or sport performance data of a user or multiple users. One such application, plug-in, or the like may relate to comparing the athletic performance of the social network system user to a benchmark or to the athletic performance of other social network system or service members. Multiple users interacting with the application may accordingly compete based on their athletic performance. The benchmark comparison and/or multiple user competition may be visually represented, in particular with the avatar(s) of the user(s).

For example, each user may select a pre-designed avatar, may customize the pre-designed avatar, or may upload or otherwise create an avatar as introduced above. Thereafter, each user may be represented by their respective avatars while interacting with and participating in the social network system or service. In an embodiment for which multiple users are competing based on their athletic performance, the competition may be visually displayed or represented by the users' avatars. In an embodiment, for example, the competition may be represented by displaying multiple avatars (i.e., of multiple social network users) in the same screen, frame, window and the like. Further, the avatar position in the frame may represent the relative athletic performance of the corresponding user compared to other users participating in the competition.

In an embodiment, the competition may represent the total distance walked, jogged, run, etc. by each user after a common starting point. It is to be understood that other performance metrics (e.g., weight lifted, calories burned, duration of aerobic training, frequency of aerobic training, etc.) may be represented by the competition. Total distance walked, jogged, or run (or other performance metric) may be represented by the horizontal or vertical position of each avatar within the screen, frame, window, and the like. For example, total distance traversed by a user may be represented by horizontal position within the screen, frame, or window, with total distance traversed increasing from left to right across the screen, frame, or window (i.e., in an increasing distance from the origin or starting point of the competition as represented by a Cartesian coordinate system). Accordingly, an avatar displayed to the right of another avatar may visually indicate that the former user is leading the latter user in the competition.

Further, the screen, frame, or window may represent a partial or zoomed view of the competition. In particular for competitions involving more than a few participants, the screen, frame, or window may only simultaneously display the progress of a portion of the participants so that the relative position of the avatars may be visually resolved. For example, the competition may represent the walking, jogging, or running progress of the users toward a goal of 100 miles. Each user's screen, frame, or window displaying their avatar may represent fewer than the 100 miles. More specifically, the screen, frame, or window of a user who has traversed 50 miles may only include the avatars of those users who have traversed 45 to 55 miles. Accordingly, that user may have a visual representation of their closest competitors. In an embodiment, the domain of a user's screen, frame, or window (i.e., width of the screen, frame, or window in miles for this example) may adjust to display only a predetermined number of avatars.

However, in an embodiment a user may alternatively or additionally wish to have a visual representation of the entire competition. For such an embodiment, a portion of the user's screen, frame, or window may include a representation of the entire competition as well as their specific location within the entirety. For example, the top or bottom of the user's screen, frame, or window may include a scroll bar or the like that allows the user to control (e.g., with a mouse click or rollover) the portion of the competition that will be displayed. Further, the scroll bar may include tick marks or other indicia of the progress of some or all of the users participating in the competition. A user may therefore know their progress compared to other users in the competition as well as having a visual representation of at least their closest competitors based on the relative position of the avatars within the screen, frame, or window. In an embodiment, the screen, frame, or window may visually respond to the user rolling over the tick marks or indicia with the display name or other identifier of the other users. The visual response may further include the progress (in an embodiment distance traversed) of the other users in addition to or in lieu of the display name or other identifier of those users. Finally, the scroll bar may include an arrow, color differentiation, or other similar pointer to the location of the individual user viewing the screen, frame, or window within or adjacent to the competition scroll bar to determine their progress in the competition.

Figure 8:
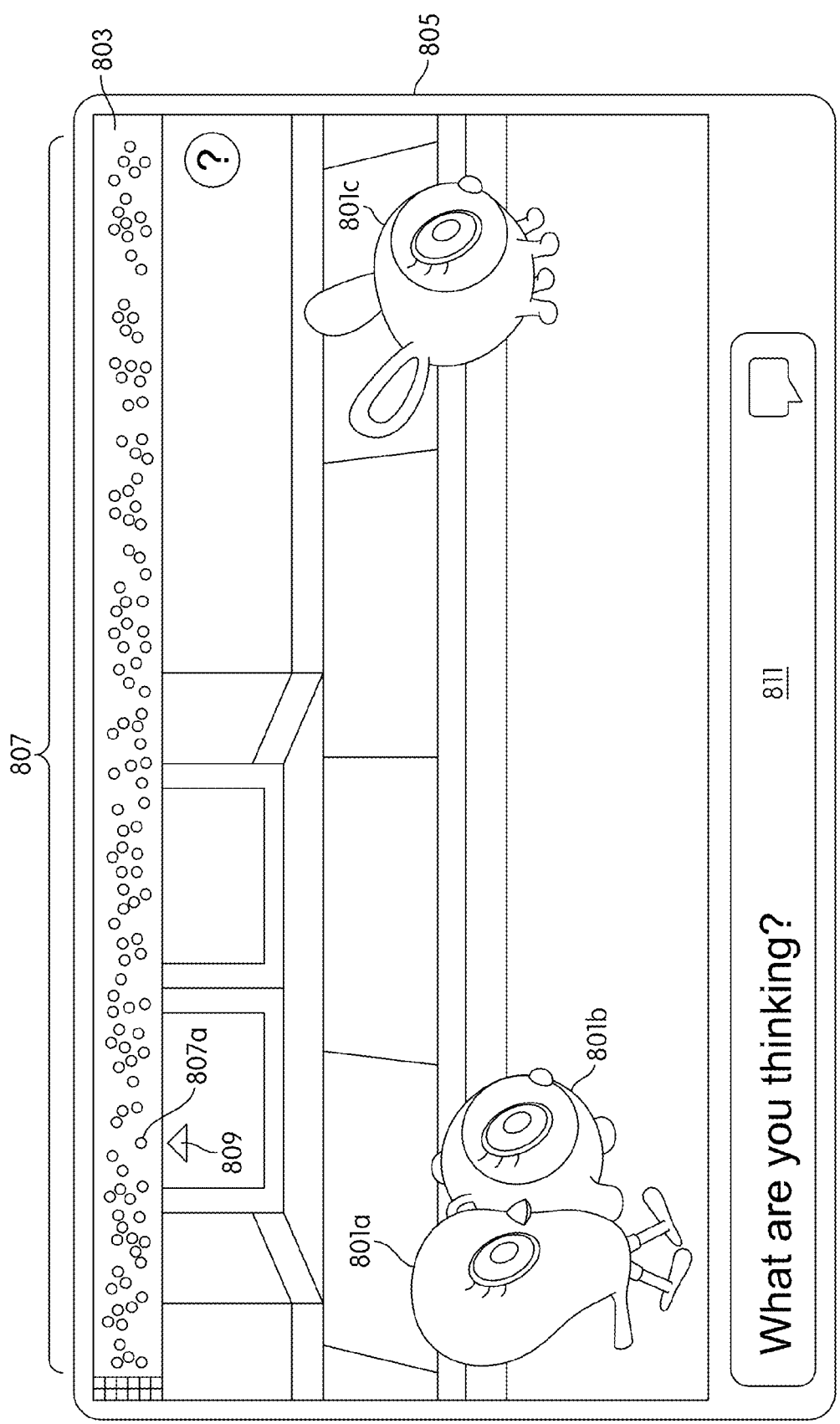
FIG. 8 illustrates a screen shot of the application of an embodiment according to one or more aspects described herein.

FIG. 8 illustrates a screen shot of an exemplary embodiment according to the description above. Three avatars 801 representing three users are displayed in various locations within the application window. More specifically, the three avatars 801 appear at various depths in the foreground against a background. In an embodiment, the background may be a running track, a street marathon course, a trail, or any other background related to walking, jogging, or running. The background may further represent a weight room, gymnasium, or any other suitably related backgrounds should the athletic performance of the user relate to weight training, aerobic training, and the like. Alternatively, the background may be completely arbitrary or whimsical to contribute to the departure of the overall avatar environment from reality. As illustrated, the middle avatar 801b represents the user who is executing and viewing the avatar application. The avatar 801c to the right represents the user immediately ahead in the competition or race while the avatar 801a to the left represents the user immediately behind in the competition or race.

The top of the application includes a scroll bar 803 representing at least a portion of the competition or race. In an embodiment, the scroll bar 803 represents the entire race from beginning to end while the remainder 805 of the window (i.e., the portion of the application window including the avatars) might only display a graphical representation of a portion of the entire race. The location of some or all of the users participating in the competition or race may be displayed in the scroll bar as tick marks, dots, or other similar indicia (e.g., ticks 807). Further, the location of the user executing and viewing the avatar application may be highlighted by an arrow 809 or other pointer. The tick mark 807a, dot, or other similar indicium may further still have a color, size, or shape that differentiates it from others. As discussed above, the user may roll over or otherwise select a tick mark, dot, or other indicium to display the corresponding, user name, identity, and/or progress within the competition or race.

In an embodiment, one or both of the background and the avatars 801 may be animated. For example, the background may scroll (in the illustrated example from right to left) as a visual cue that the avatars 801 represent users' progress in walking, jogging, or running during a race or competition. Further, the avatars 801 may appear to be walking, jogging, running, or otherwise in motion. More specifically, the avatar animation may relate to the athletic performance of the user represented by the avatar. For example, a user who has run frequently, with substantial duration, and/or a substantial distance may be represented by an avatar whose animation mimics or suggests a fast running pace. Conversely, a user who has walked infrequently with little duration and/or distance may be represented by an avatar whose animation mimics or suggests a slow walking pace. In an embodiment, an inactive user may even be represented by an avatar sitting down or otherwise lacking animation. The animation of the avatar may reflect the most current athletic performance of the user (e.g., within a particular time period) or may reflect an average (including a moving average) over the duration of the entire race or competition. Accordingly, the avatar animation may reflect a trend in the corresponding user's athletic performance in addition to or in lieu of their position in the overall race.

While participating in the race or competition, a user may generate a comment by inputting text and/or symbols in a comment entry box. As illustrated in FIG. 8, the comment entry box 811 (in an embodiment containing the prompt "What are you thinking?") is located adjacent to and below the race or competition area defined by the background and the avatars 801 superimposed thereon. When a user inputs a comment in entry box 811, a dialogue box, bubble or the like will pop up or otherwise appear adjacent to the avatar within the application representing the user from whom the comment initiated.

Figure 9:
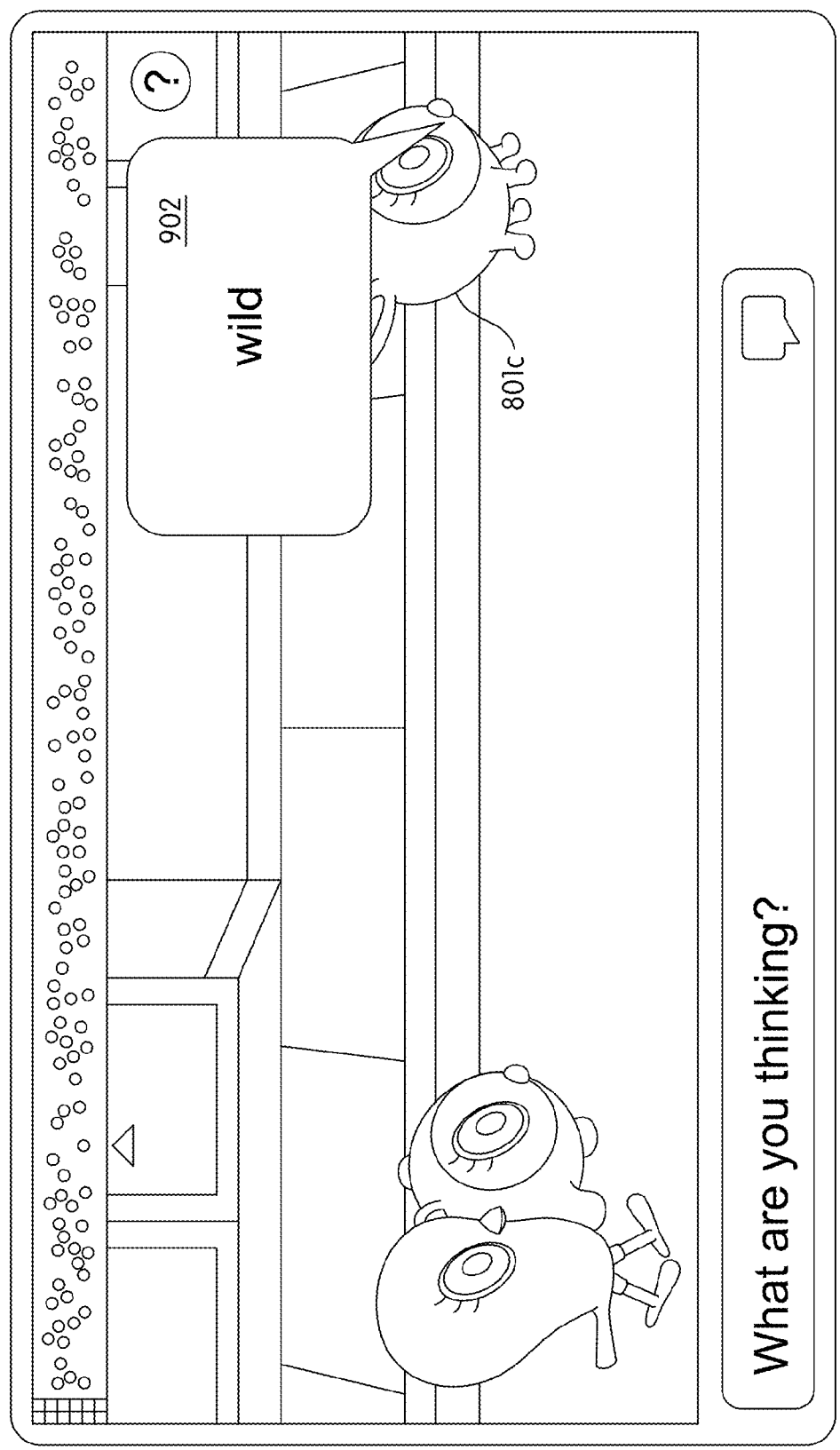
FIG. 9 illustrates an alternate screen shot of the application according to one or more aspects described herein.

FIG. 9 illustrates a dialogue bubble 902 appearing and extending from avatar 801c upon entry of a comment (i.e., "wild") submitted by the user associated with avatar 801c. In an embodiment, the comment will be visible to other users whose avatars are in the same window or frame of the race or competition. Further, an indication (not shown) may appear in the scroll bar should a user post a comment whose avatar is not within the same window or frame of the race or competition. Any user may then roll over or select the tick mark, dot, or other similar indicium of the commenting user/avatar to review the comment. In another embodiment, additional avatars may be introduced into a race or competition representing professional athletes or in the form of "avatar trainers" that may offer motivational messages or other commentary.

In addition to the current position or standing, the avatar application may also display standings, a leader board, trophies, and the like depending on the outcome of a race or competition. Further, the avatar application may display milestones, achieved goals, and the like for a user who is not part of a race or competition but has otherwise established personal achievement benchmarks.

As noted, the avatar position, appearance, and/or animation may reflect the athletic performance of the user. The user's athletic performance may in turn originate in a variety of ways. In an embodiment, the user may input their athletic performance. For example, the user may input a particular distance run in a particular time for each instance of aerobic activity. They may alternatively or additionally input pounds lifted, games played, and the like depending on the nature of the race, competition, or comparison to benchmarks or goals.

According to another aspect, the avatar module may communicate with one or more athletic performance databases or other athletic performance data collection modules or utilities. For example, numerous Internet-based or online services collect athletic performance data from users. In particular, certain Internet-based or online services may interoperate with sensors or other recording devices that a user may wear or carry while working out, walking, jogging, running etc. In an embodiment, the athletic performance data may be collected with an accelerometer, pedometer, heart rate monitor, calorie monitor and the like as are known in the art.

Non-athletes or users not represented by an avatar within the race or competition may also execute the application and interact with the athletes or users represented by an avatar within the race or competition. For example, a non-athlete or user not represented by an avatar within the race or competition may send or post messages or comments, deliver gifts, or otherwise communicate with one or more athletes or users represented by avatars within the race or competition. Further, the non-athlete or user not represented by an avatar within the race or competition may establish goals or milestones for an athlete.

Figure 10:
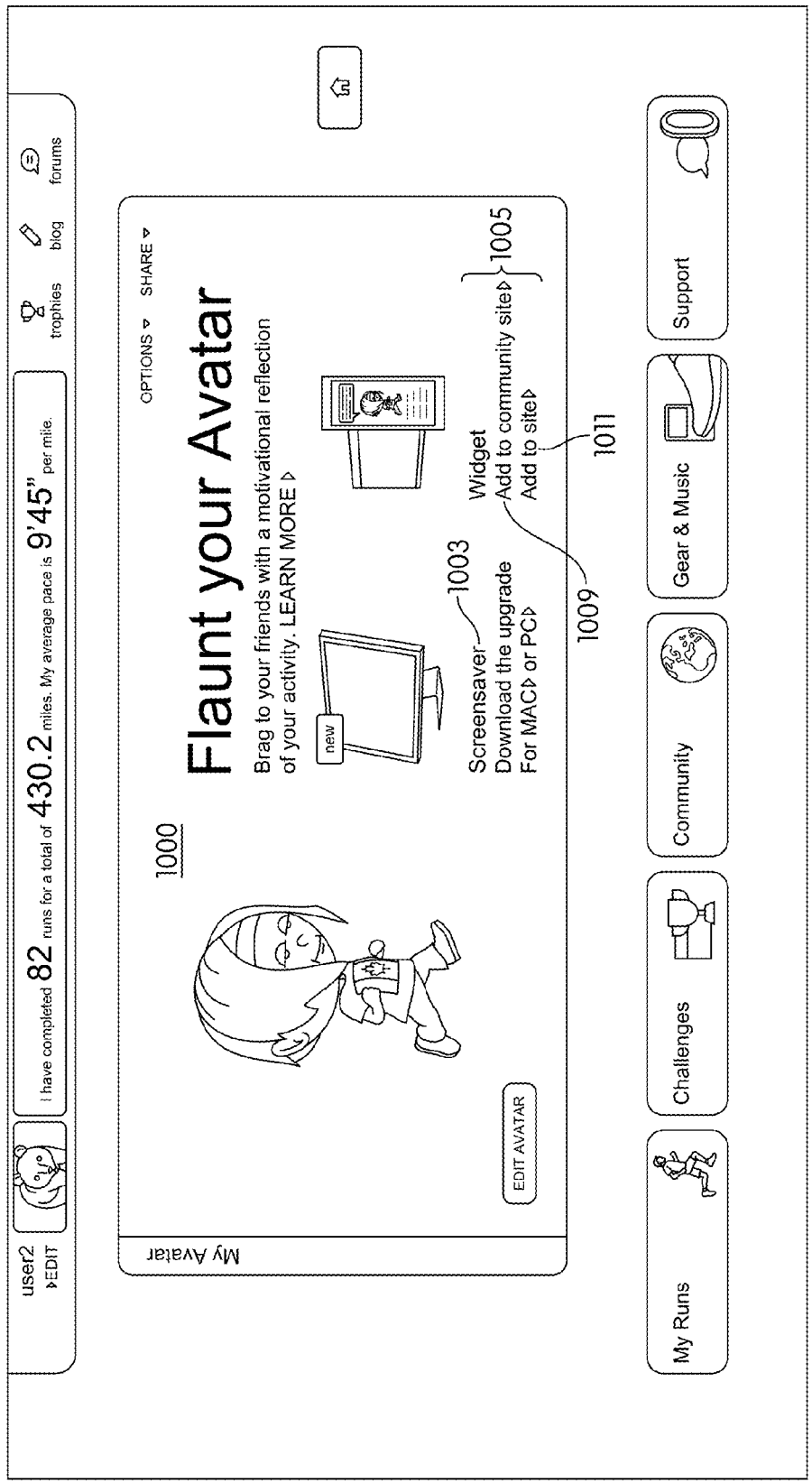
FIG. 10 illustrates an avatar publishing interface according to one or more aspects described herein.

Users may further use their avatars in other social networking systems and services. For example, a user may elect to publish an avatar to a social networking website such as FACEBOOK. FIG. 10 illustrates a publishing interface 1000 through which a user may elect to publish and download a screensaver featuring the user's avatar through option 1003 or to generate a widget that may be included in various sites using option 1005.

Figure 11:
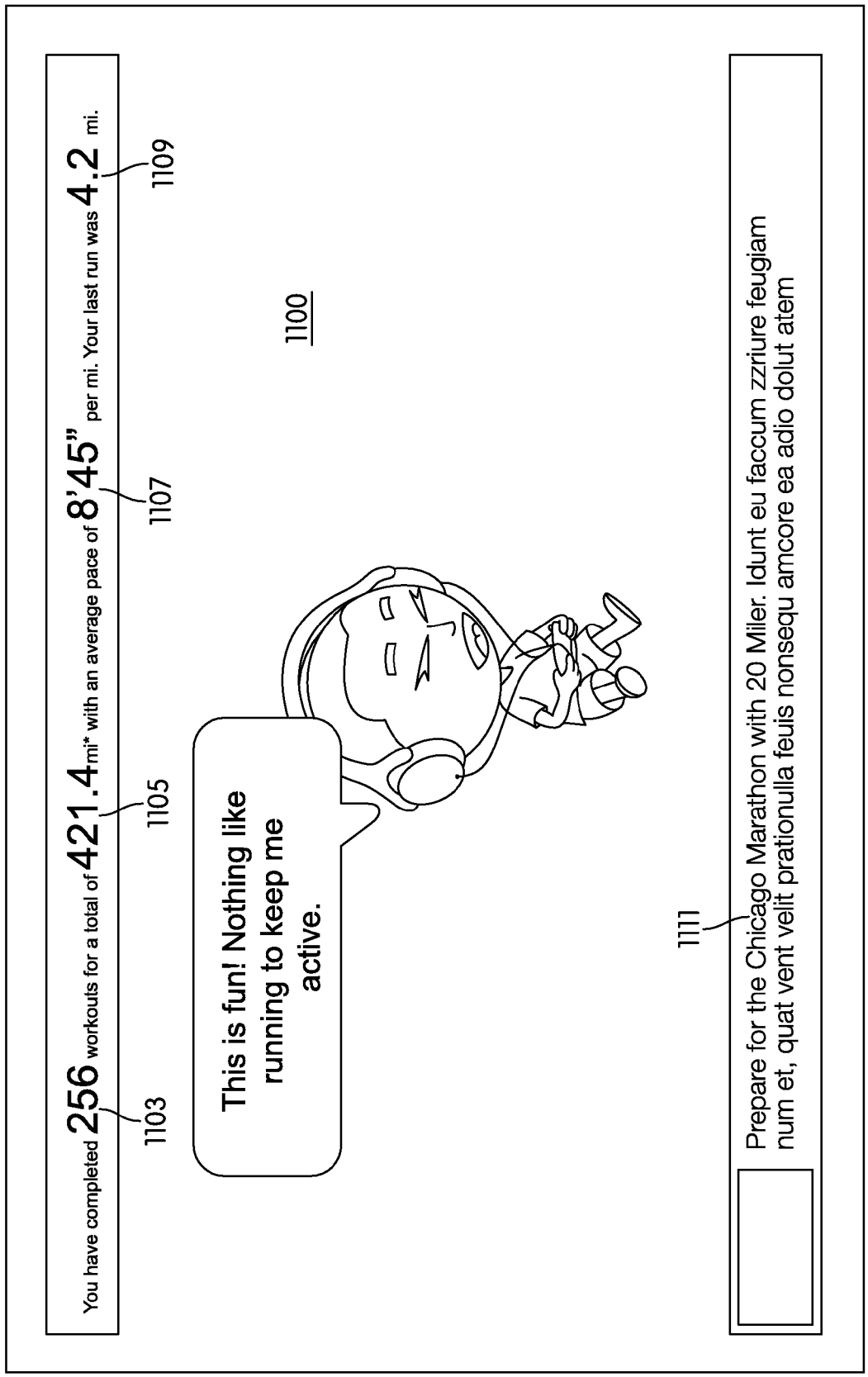
FIG. 11 illustrates a screensaver showcasing an avatar according to one or more aspects described herein.

FIG. 11 illustrates a screensaver featuring a user's avatar and athletic performance information. Screensaver 1100 may further include athletic performance statistics of the user associated with the avatar. The athletic performance statistics may be updateable, e.g., by downloading a new screensaver periodically or aperiodically or dynamically by retrieving data from a network site. For example, statistics may include number of workouts completed 1103, distance run/walked 1105, average page 1107 and distance of last run 1109. Screensaver 1100 may further include announcements or notifications of upcoming events 1111.

Referring to FIG. 10, option 1003 may include two different links to suit MAC users and PC users. In one example, a zip file may be generated and downloaded for MAC users while a .exe file may be generated and downloaded for PC users. Widget option 1005 may include a direct link 1009 for adding an avatar widget to a specific social network site such as FACEBOOK as well as a generic link 1011 for adding an avatar widget to other sites. A widget generally refers to an interactive component of a user interface that typically is generated using a portable segment of code that may be separately installed and executed.

Direct link 1009 may differ from generic link 1011 in that direct link 1009 may automatically add the code segment corresponding to an avatar widget to the specific social network site. The code may be pre-configured for the social network site and thus, might not need user interaction for installation into the user's social network page in the particular site. In one or more configurations, the user might need to login to his or her social network page prior to installation using direct link 1009. Generic link 1011, on the other hand, might require the user to self-navigate to a location in the social network site where code segments or executable code such as applets maybe added. According, choosing generic link 1011 may generate an interface where a user is able to obtain a copy of the widget code.

Figure 12:
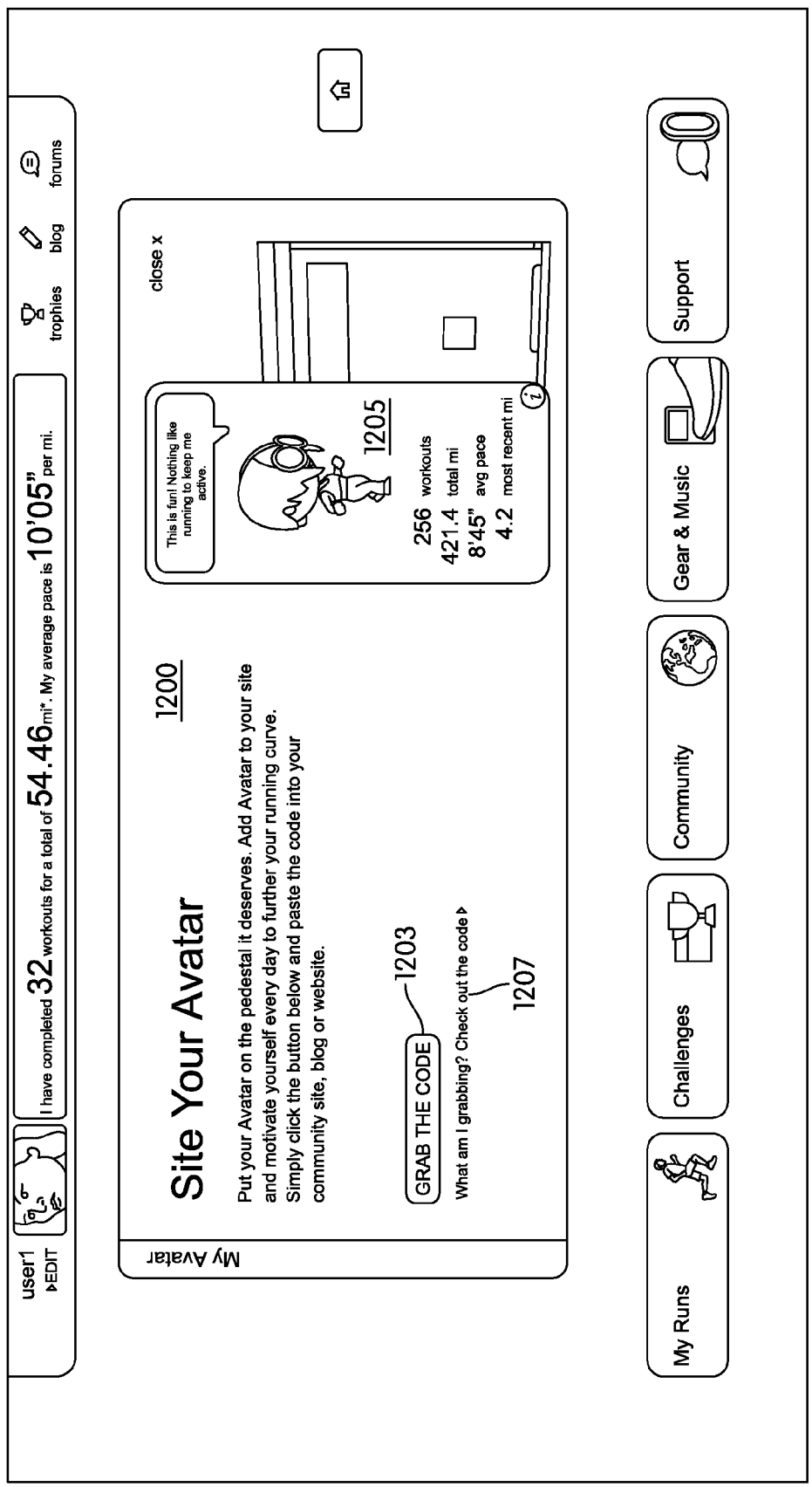
FIG. 12 illustrates a code retrieval interface according to one or more aspects described herein.

FIG. 12 illustrates a code retrieval interface 1200 where a user may obtain code for placing an avatar widget on a site. Selecting "GRAB THE CODE" option 1203, for example, may automatically cause the user's device to copy the code segment onto a clipboard. Alternatively, a user may select the "check out the code" option 1207 that causes the code to be displayed in interface 1200. The user may then manually copy the code from interface 1200. A sample widget 1205 may be displayed in another portion of interface 1200 to illustrate the appearance of the widget generated using the code. In one or more arrangements, widget code includes MACROMEDIA FLASH code.

Figure 13:
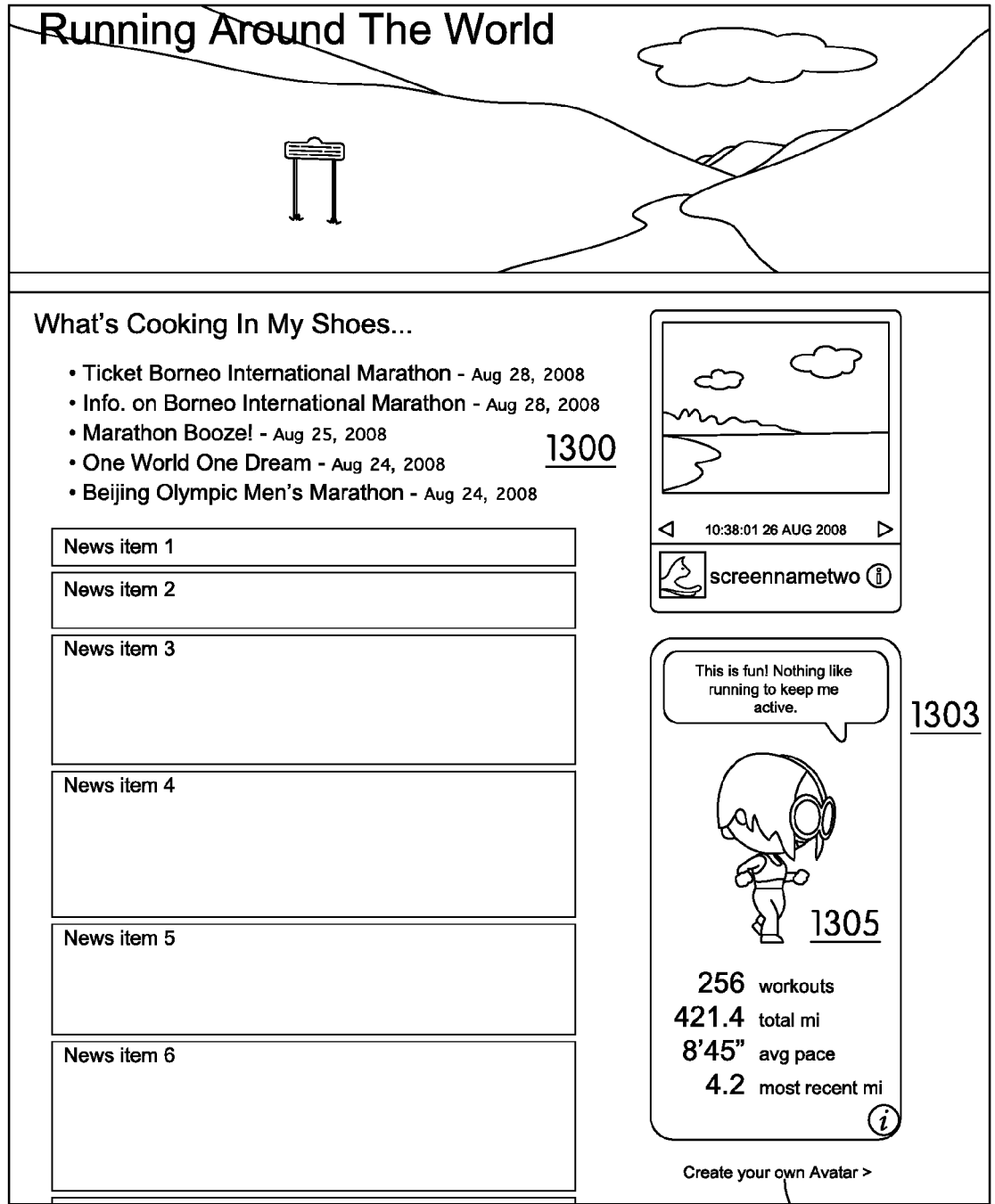
FIGS. 13 and 14 illustrate example avatar displays according to one or more aspects described herein.

FIG. 13 illustrates an example website after the addition of avatar widget code. Webpage 1300 may generally provide information about various topics such as running events and trails in different countries. A user wishing to add an avatar widget to webpage 1300 may do so in a desired portion of the page such as portion 1303. Upon inserting the code, avatar widget 1305 may be generated and appear in portion 1303. Avatar widget 1305 may include athletic information and statistics of the webpage owner or publisher including workouts performed, mileage run, average page and most recent miles run. An additional option 1307 for creating your own avatar may be displayed below the widget to provide viewers the option of starting their own avatars and tracking their own athletic performance.

Figure 14:
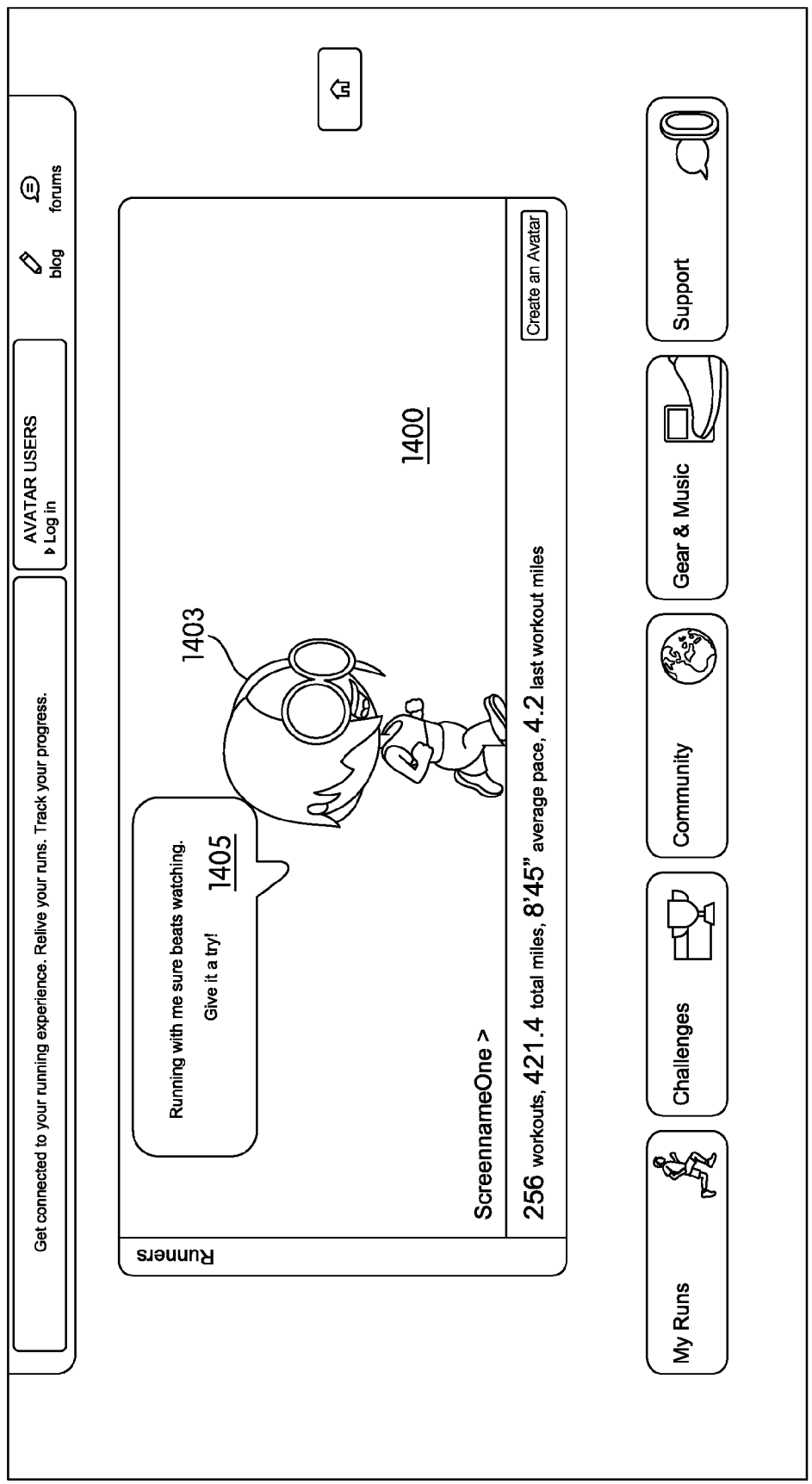

FIG. 14 illustrates an interface providing an alternate view of an avatar. In particular, interface 1400 may be provided at the host site supporting the avatar and athletic performance tracking features. Interface 1400 may provide information similar to that provided in avatar widget 1305 of FIG. 13. Additionally, interface 1400 may display avatar 1403 with a speech bubble 1405. Speech bubble 1405 may include commentary that is selected from a predefined selection of comments. The selection of comments may be grouped or organized based on an athletic activity. Commentary may be selected from a selection of runner comments if the user corresponding to avatar 1403 is an avid runner. An athletic performance site or application may determine a relevant sport or activity based on the athletic performance data received from the user. For example, if a user enters weight-lifting records, goals, challenges and/or other data, the site may identify the user as a weightlifter and choose appropriate commentary/speech bubbles.

FIG. 15 illustrates an interface for adding an avatar widget to a user's page in social network site FACEBOOK. Interface 1500 may be generated by the social networking site and request identifying information such as a screen name registered with the avatar site. Specifically, interface 1500 may include an entry field 1503 for specifying the user's avatar site screen name. The social network site may have a hook or communication protocol with the avatar site to locate and retrieve avatar widget code based on identifying information such as a user's screen name. Interface 1500 may further include an option 1505 to create an avatar. Option 1505 may, for example, link the user to the avatar site for creation of an account and avatar. Once the user enters his or her avatar site screen name and the social networking site is able to locate the screen name, the user's avatar may be added to his or her social networking site page. Various error or warning messages 1507 may be displayed if, for example, a user's avatar is set to private or if the screen name was not found in the avatar site.

Figure 16D:
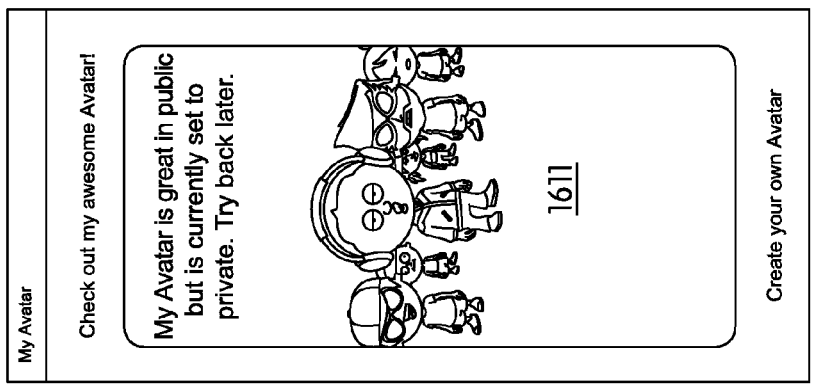
FIGS. 16A-16D illustrate example avatar widgets according to one or more aspects described herein.
Figure 16C:
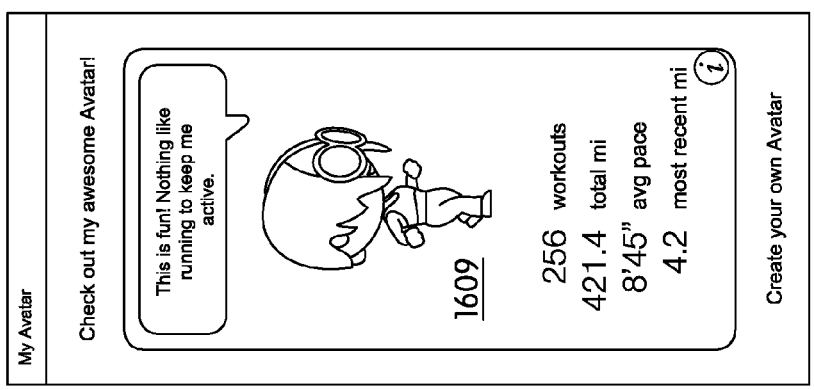
Figure 16B:
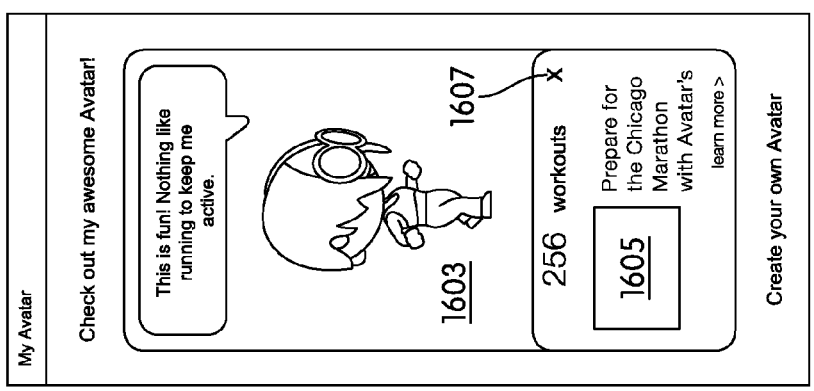
Figure 16A:
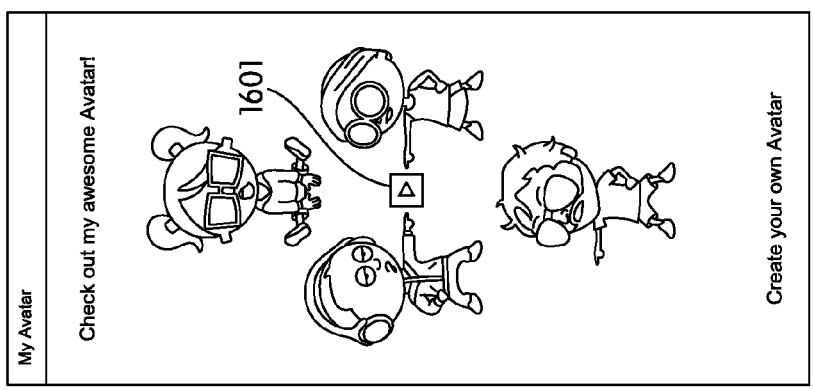

FIGS. 16A-D illustrate different versions of an avatar widget that may be placed on a social networking site/page. FIG. 16A illustrates a default avatar widget view that may be presented to a viewer upon first loading a user's social networking page. The default view may allow a user to control whether or not to execute the avatar widget code. By selecting, e.g., the play option 1601, the avatar widget code may be executed and an avatar widget specific to the social networking page's owner may be generated. For example, FIG. 16B illustrates an avatar widget 1603 that includes a message 1605 from one or more other sites or event sponsors. The special message may include an advertisement, an invitation to join an event, a community service announcement and the like. The viewer may choose to ignore the message by selecting close option 1607. When open, message 1605 may hide other information such as the social networking page owner's athletic performance statistics and other information. Once message 1605 is closed, the information may be displayed. FIG. 16C illustrates an avatar widget 1609 that is configured to display the athletic performance data without a special message such as message 1605 of FIG. 16B.

In FIG. 16D, if a social network page owner has set their avatar and avatar widget to private, an alternate avatar widget or image 1611 may be displayed to a viewer. Widget or image 1611 may include a message notifying the viewer that the avatar is set to private. Setting an avatar widget or avatar to private may indicate that the owner only wants a certain select group of people to be able to view the owner's widget and athletic performance information or that no one may see the widget or avatar except for the owner.

According to one or more aspects, just as an avatar from an athletic performance monitoring site may be placed into a webpage or website, an avatar from a separate webpage or network site (e.g., a social networking community) may be dropped into and used in the athletic performance monitoring site. Thus, instead of or in addition to creating an avatar within the athletic performance monitoring site, a user may use his or her avatar from a social network community. The user may then receive awards and gifts that modify the avatar's appearance or other attributes. In one example, avatars may be transferred as a file such as an image file. In another example, avatars may be defined and transferred as 3D models.

Figure 17:
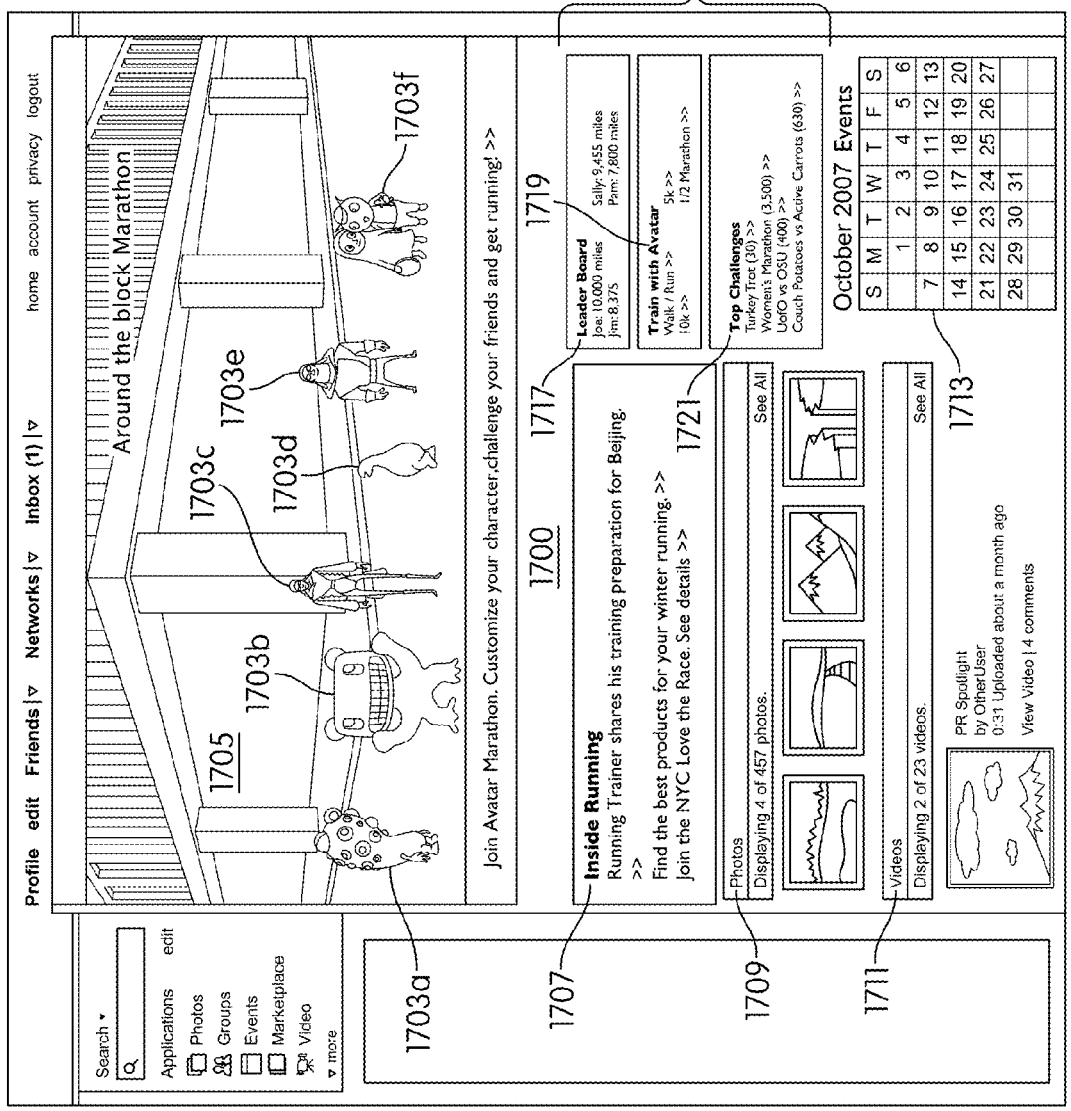
FIG. 17 illustrates a community or group of a social networking site according to one or more aspects described herein.

FIG. 17 illustrates a social networking community or group page 1700 that includes members whose avatars 1703 may be displayed in an avatar display area 1705. Avatar display area 1705 may include a background that is representative of an activity, a location or some other type of image. For example, display area 1705 has a street view background that may correspond to an "around the block" marathon theme. Other types of images or backgrounds may include an image of a desk top, a retail store and the like.

Community page 1700 may further include announcements about members, events, news and the like in announcements section 1707. Additionally, photos and videos may be included in page 1700 in photo section 1709 and video section 1711, respectively. Photos, videos, news, events and the like may be posted by community or group members or through a news, photo, video or event feed from another site or organization (e.g., a marathon sponsor). A calendar 1713 may be provided to allow members to track various events that are occurring in the near future. For example, since page 1700 is dedicated to marathon running, calendar 1713 may highlight dates in which marathon events are occurring. Data section 1715 may provide several types of information including a leader board 1717 that displays the top performances of group members, training options 1719 providing links or information about training, and challenges 1721 listing challenges that are currently available for joining. Leader board 1717 and challenges 1721 may retrieve and display live information feeds from a sponsor site that, for example, tracks athletic performance information, user created and/or issued challenges and the like.

Figure 18:
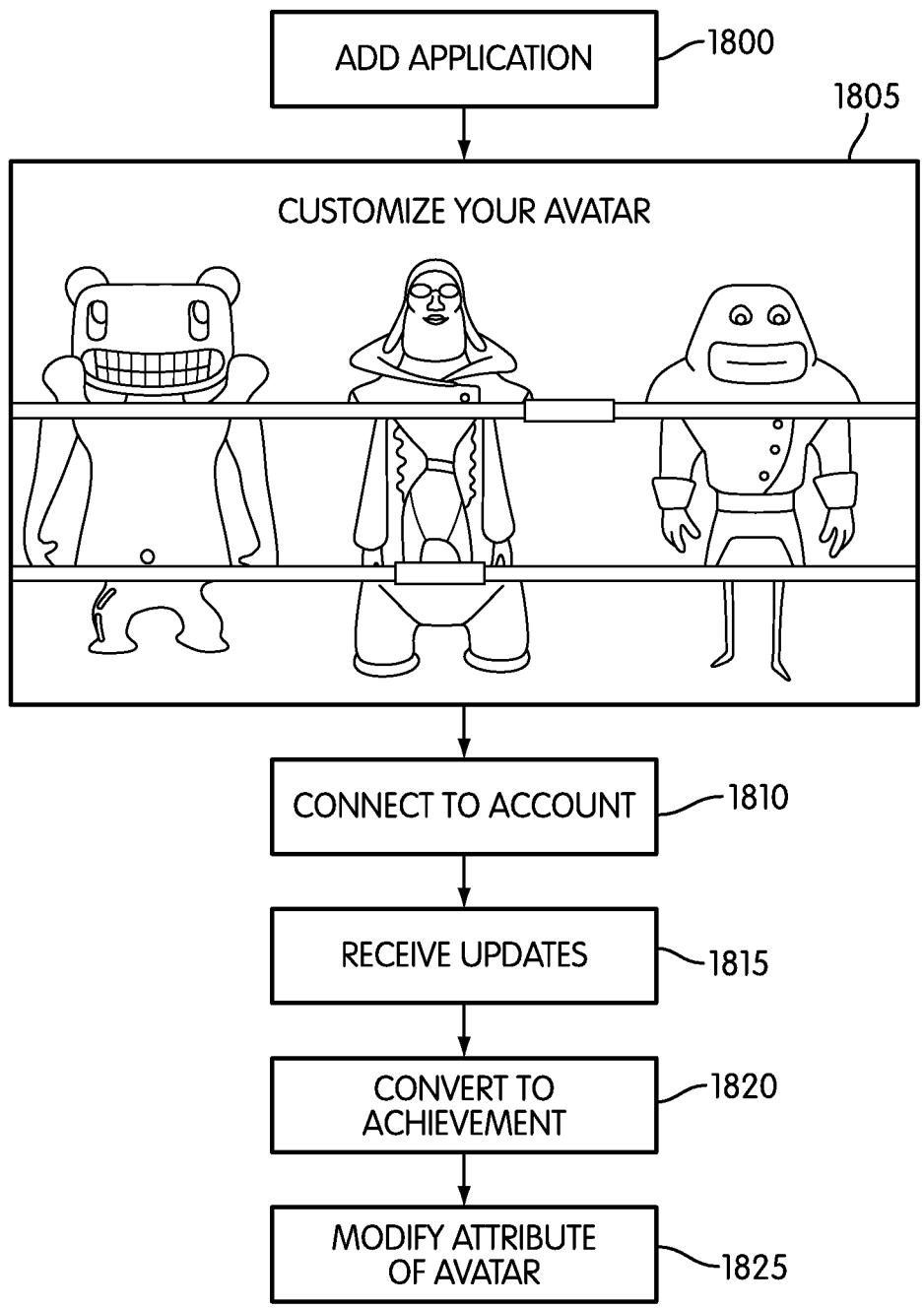
FIG. 18 illustrates an example method for creation and addition of an avatar to a social networking site according to one or more aspects described herein.

In one or more configurations, avatars 1703 displayed in avatar display area 1705 may be created specifically for the social networking site's community page 1700. FIG. 18 illustrates a process by which a user may create an avatar in the social networking site for linking to an athletic performance site. In step 1800, for example, a user may add an athletic performance application to his or her social networking page or account. This may include adding code to their page or authorizing new information to be displayed in or associated with the user's social networking account. In step 1805, the user may be asked to create or customize their avatar. Various methods for creating an avatar may be used including allowing a user to select between and assemble predefined head, upper body and lower body portions. Once the user's avatar has been created, the user may then connect or associate the avatar to an athletic performance monitoring site in step 1810. The athletic performance monitoring site may be configured to receive performance data from a user's athletic performance monitor device (e.g., a pedometer, accelerometer, heart rate monitor or other type of sensor) and to log that information in a database in association with the user. In step 1815, the social networking site may receive updates to the user's athletic performance. The user's athletic performance (e.g., steps taken or miles run) may be translated into some achievement in the social networking site's environment in step 1820. For example, a number of miles run may be converted into a certain distance to move the user's avatar in a community page (e.g., relative locations of avatars 1703 in page 1700 of FIG. 17). In another example, a user's avatar's size may increase based on the number of miles run or other goals reached by the user. Accordingly, in step 1825, an avatar's appearance, location or disposition may be altered based on the updated athletic performance information.

Figure 19:
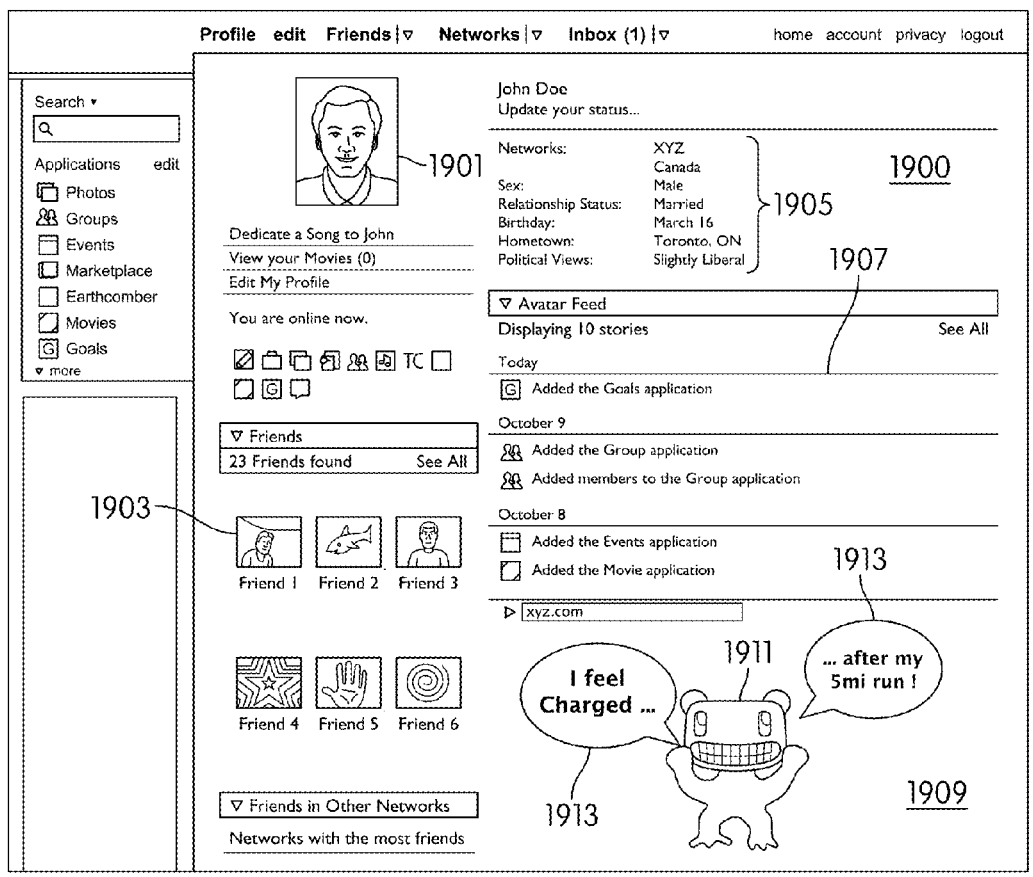
FIGS. 19 and 20 illustrate example avatar display sections in a social networking site according to one or more aspects described herein.

FIG. 19 illustrates a personal social networking site page that includes an athletic performance avatar. Page 1900 may include a variety of information including a picture 1901 or other image associated with the user, a listing of friends 1903, personal information 1905, an information feed 1907 and avatar section 1909. Personal information 1905 may provide information such as networks the user is a member of, relationship status, gender, birthday, hometown and political views. Information feed 1907, on the other hand, provides a log of events associated with the user. For example, if the user adds a new friend or a new application, that event may be recorded and displayed in information feed 1907. In another example, if a user changes one or more pieces of personal information 1905, that change may also be recorded and noted in information feed 1907. In yet another example, if a user achieves some athletic goal, that information may also be displayed in feed 1907.

Avatar section 1909 may include an avatar 1911 that represents a user's athletic performance and/or goals. Avatar 1911 may change expressions or body positions based on a current athletic mood or status of the user. In one example, if a user has not performed athletic activity in the past week, avatar 1911 may assume a lazy, sluggish or depressed appearance. If, on the other hand, the user has just worked out or has worked out consistently for a month, avatar 1911 may have a happy, excited or energized appearance. Alternatively or additionally, avatar 1911 may be associated with speech bubbles 1913 that provide a further expression of the avatar's mood and/or the user's athletic performance.

Figure 20:
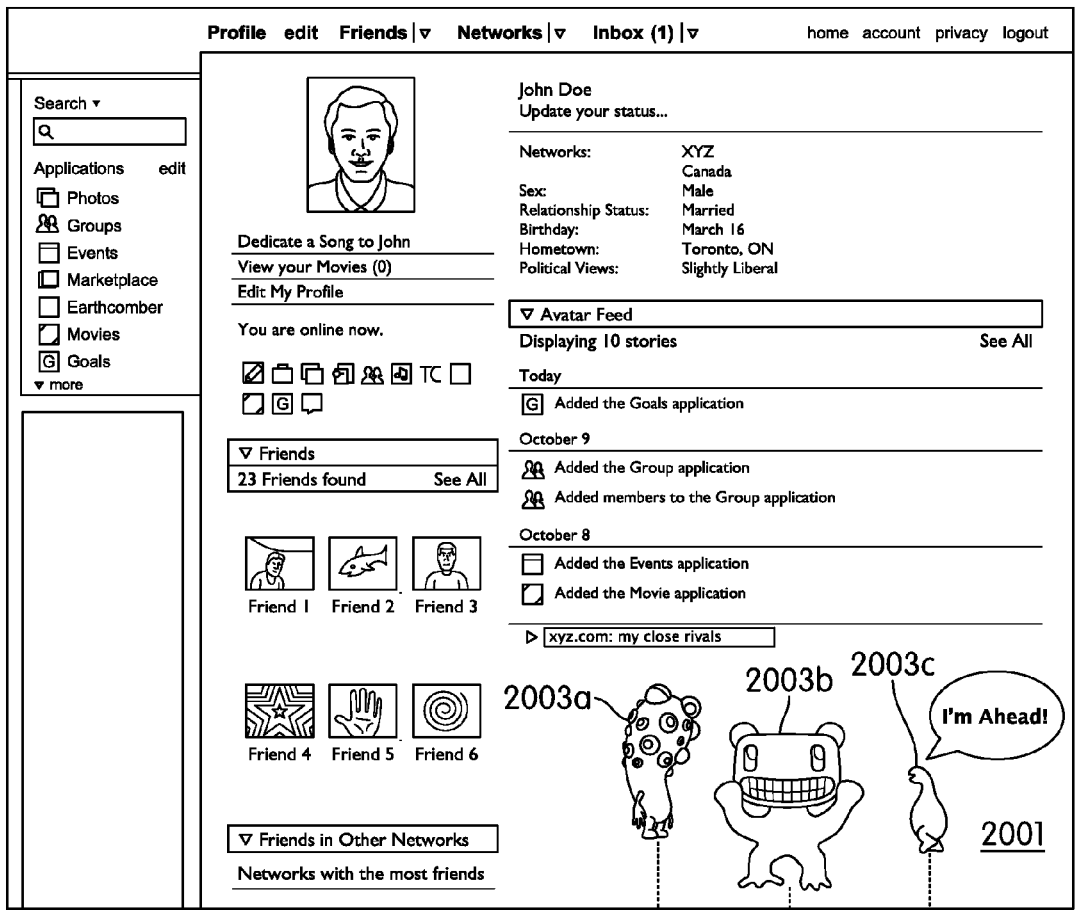

In an alternate embodiment, as illustrated in FIG. 20, an avatar section 2001 may include multiple avatars 2003 that correspond to the user and his or her friends. The relative positions between the avatars 2003 may signify a relative level of athletic achievement or athletic performance. Avatar section 2001 may display multiple avatars 2003 if, for example, the user is currently involved in a challenge or some other competition. Alternatively, avatar section 2001 may display multiple avatars 2003 based on user preference. The user may also choose which avatars (i.e., which friends) to display in avatar section 2001. The positions and other characteristics of avatars 2003 may automatically update based on live athletic performance data feeds from an athletic performance monitoring site or application linked to avatars 2003 and the social networking site.

Figure 21:
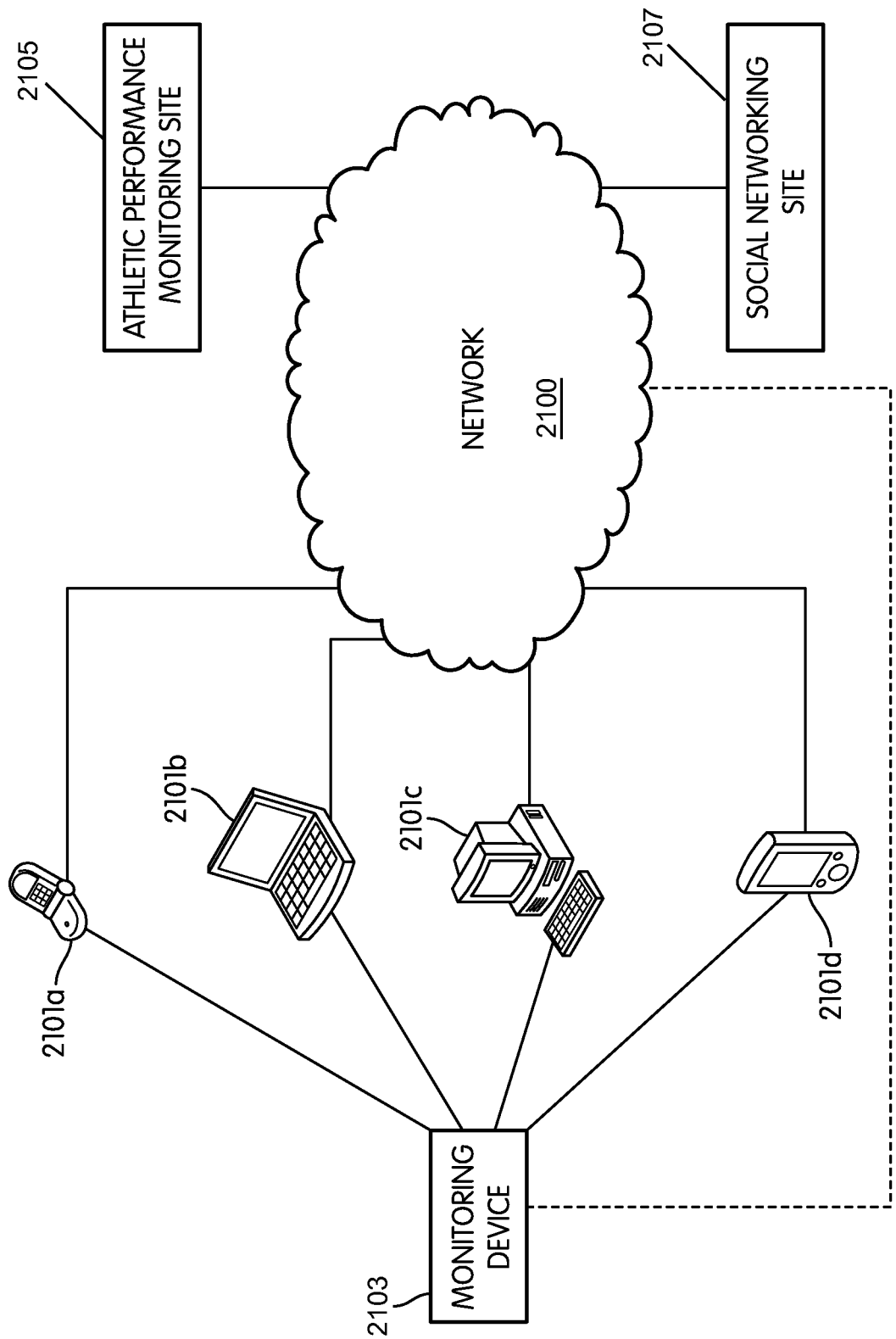
FIG. 21 illustrates a block diagram of a network connecting a social networking site, an athletic performance site and client devices according to one or more aspects described herein.

FIG. 21 illustrates a block diagram of a network in which an athletic performance monitoring site may be linked to a social networking site and user devices. User devices 2101 may include a personal computer (PC), a mobile communication device such as a cell phone or smartphone, a personal data assistant (PDA) and the like. User devices 2101 may include or may be connected to one or more athletic performance monitoring devices 2103 such as a pedometer, accelerometer, heart rate monitor, GPS device or other type of device (e.g., to determine a distance run or walked). Athletic performance monitoring device 2103 may upload athletic performance data to user devices 2101 for transmission to an athletic performance monitoring site such as site 2105 through network 2100. Alternatively, athletic performance monitoring device 2103 may transmit such data directly to network site 2105 if device 2103 includes communication components. As discussed, an athletic performance monitoring site 2105 may record athletic performance data and provide various metrics, goals, challenges, awards and the like based on the received performance information. Additionally, monitoring site 2105 may be linked to social networking site 2107. The link may be a permanent connection or may be a connection that is established periodically for updates. In one example, monitoring site 2105 may update social networking site 2107 with athletic performance data as well as an appearance of an avatar associated with the athlete. Updates may be provided on a predefined schedule, upon changes being made, upon receiving new data, at the request of a user and/or combinations thereof.

Figure 22:
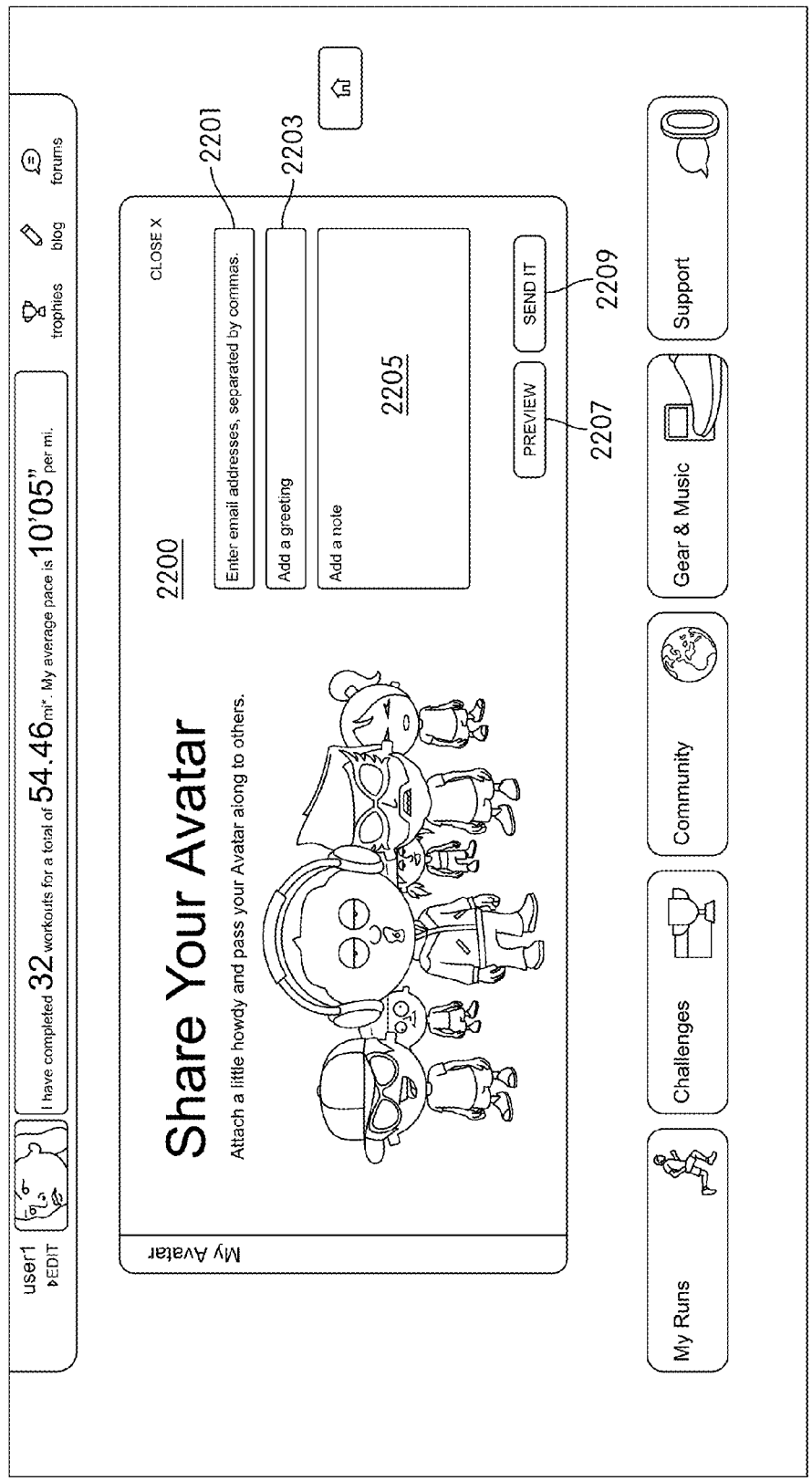
FIG. 22 illustrates an example avatar sharing interface according to one or more aspects described herein.

Avatars, as described herein, may further be shared with friends or other individuals. FIG. 22 illustrates an avatar sharing interface 2200 that allows a user to specify an e-mail address 2201 to which a message sharing the user's avatar is to be sent. Interface 2200 might further include a field 2203 for inserting a personalized greeting as well as a field 2205 for a personalized note or message to the recipient. Interface 2200 further provides a preview option 2207 to confirm the appearance of the message prior to sending and a send option 2209 for sending the invitation message.

Figure 23:
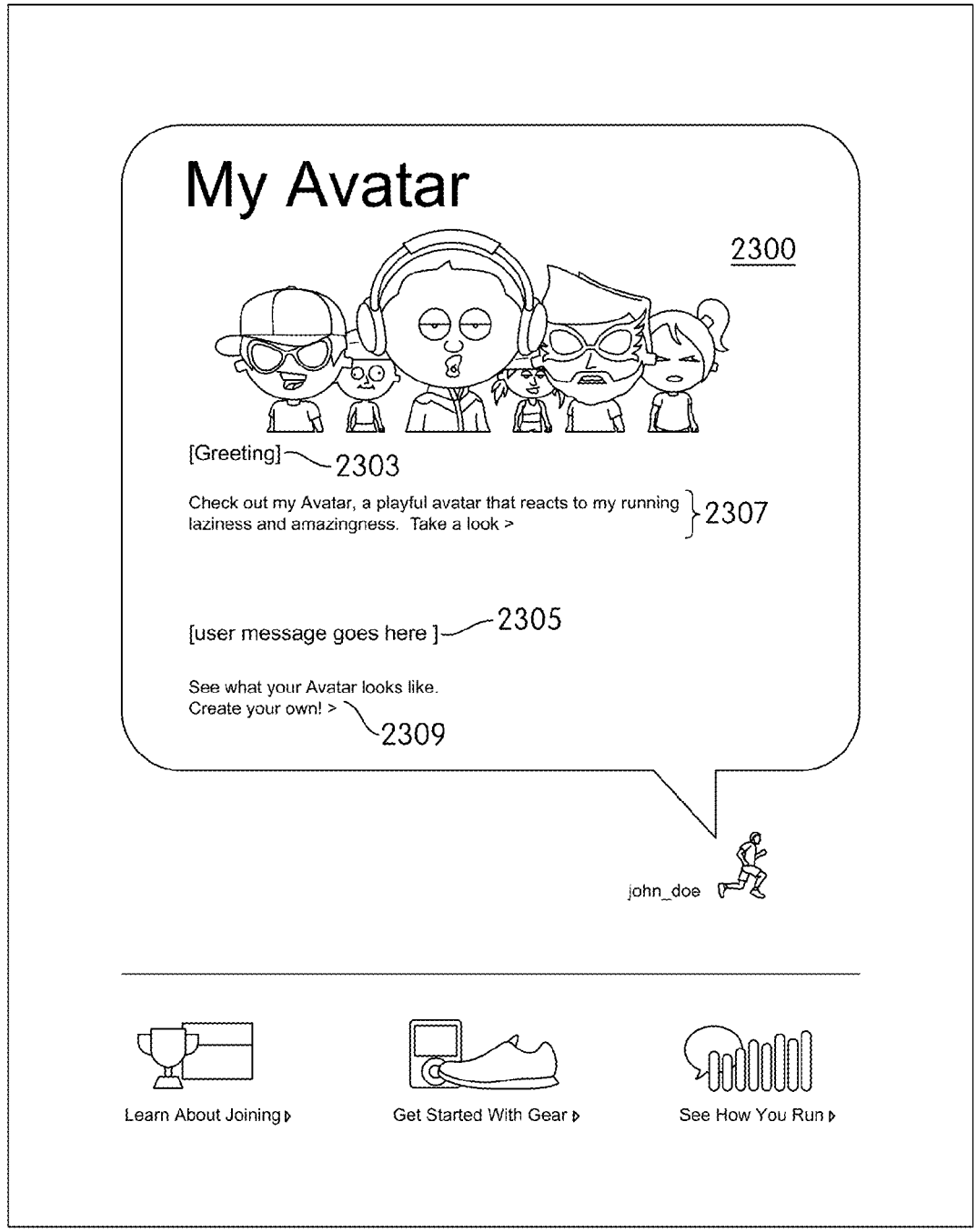
FIG. 23 illustrates an example avatar sharing message that a recipient may receive according to one or more aspects described herein.

FIG. 23 illustrates an avatar sharing message 2300 that a recipient may receive. The message 2300 may provide a greeting 2303, a personal message 2305 and a standard message 2307 including a link to the sender's avatar. Additionally, an option 2309 may be provided to allow a recipient to create their own avatar.

Figure 24:
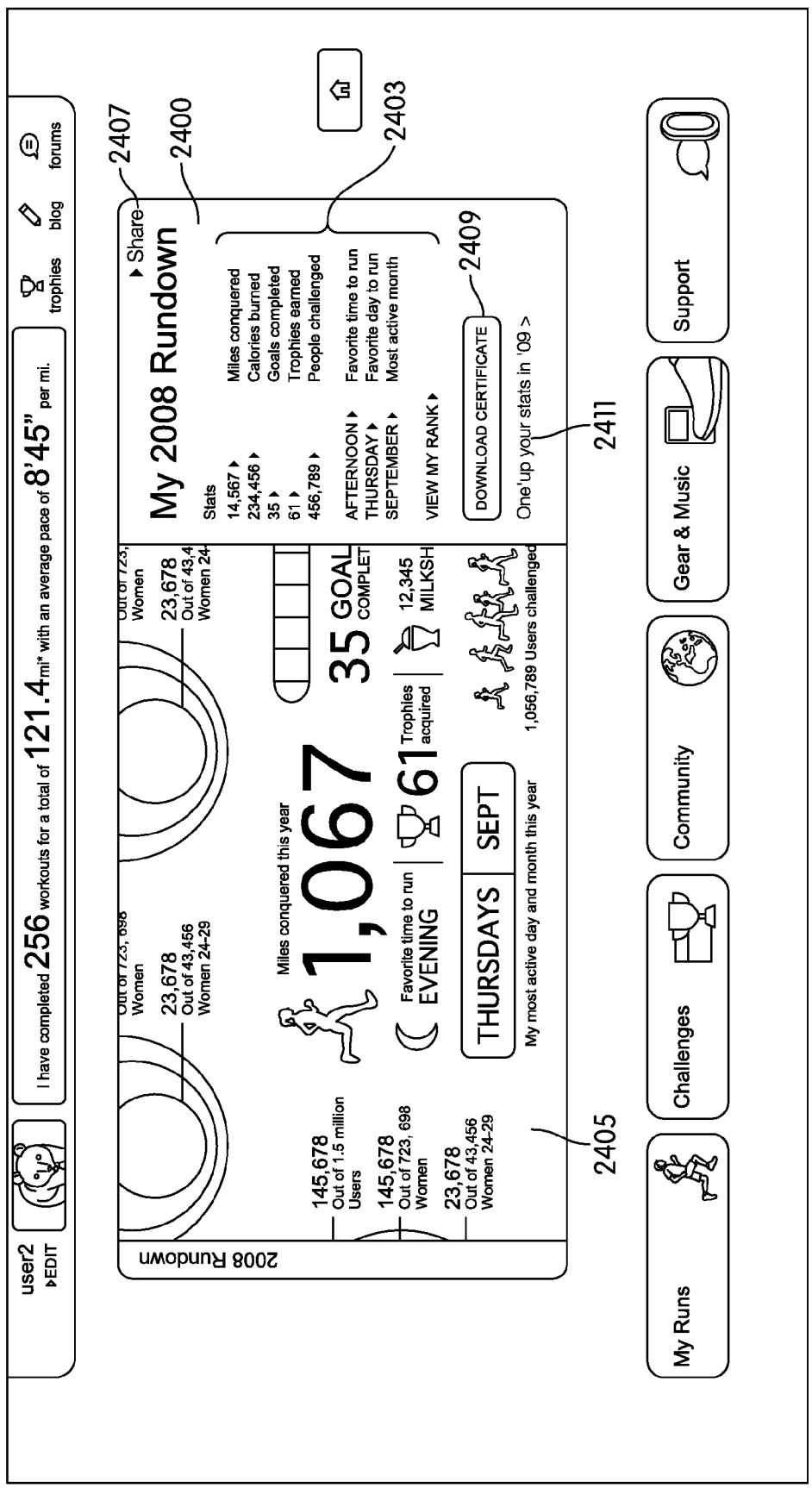
FIG. 24 illustrates an example performance summary report according to one or more aspects described herein.

FIG. 24 illustrates a performance rundown interface 2400 for a specified period of time (e.g., a past year). Rundown interface 2400 includes various statistics and information 2403 such as miles run/conquered, calories burned, goals completed, trophies earned, people challenged, favorite time to run, favorite day to run and most active month. Statistics and information 2403 may further be illustrated or depicted in panel 2405. An option 2407 to share the information may be provided as well as a download certificate option 2409 to receive a certificate for the user's accomplishments. Additionally, a user may choose to set a resolution or goal for the next year using option 2411 that exceeds the accomplishments of the past year.

Figure 25:
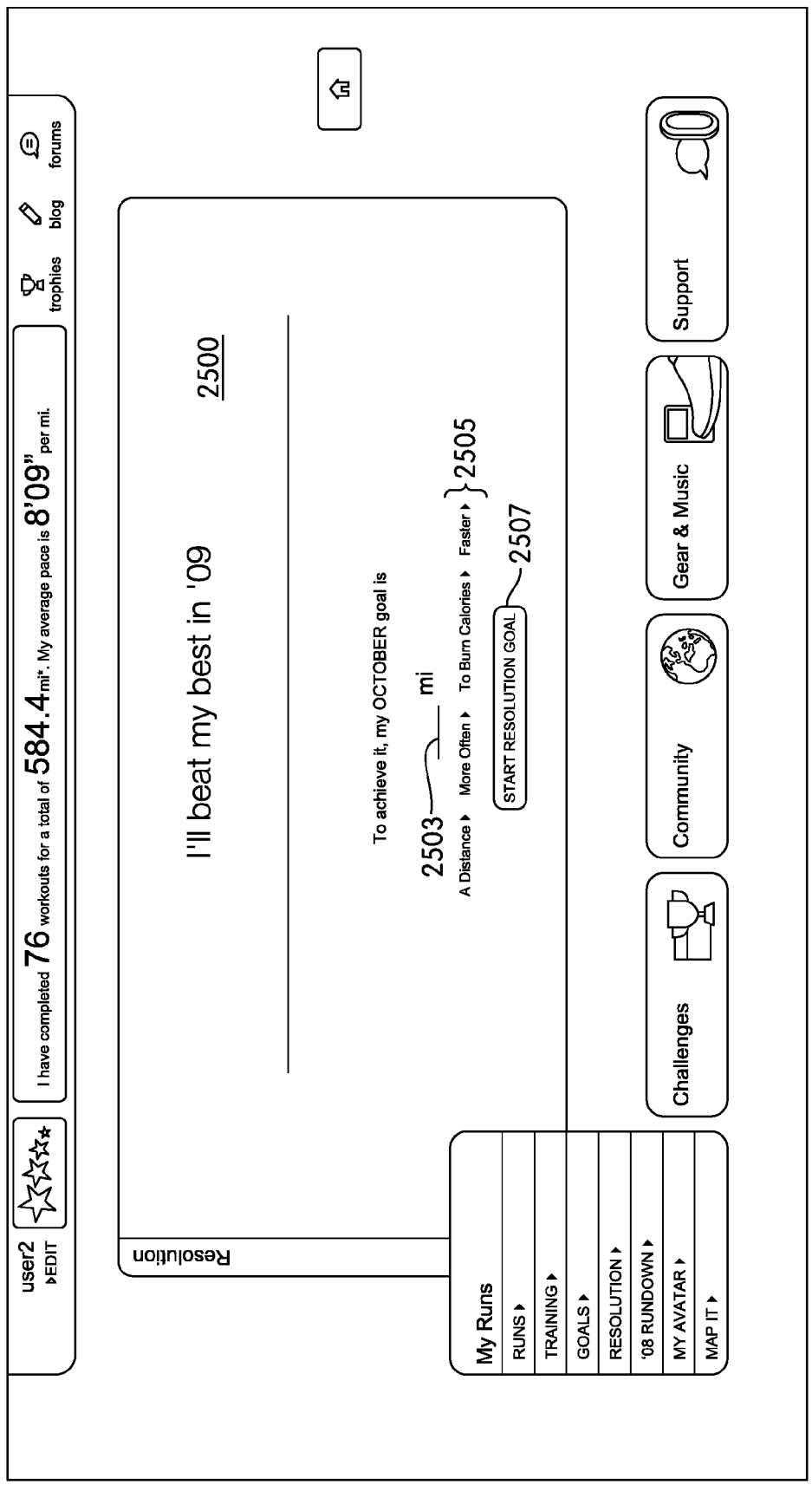
FIG. 25 illustrates an example interface for specifying a goal or resolution according to one or more aspects described herein.

FIG. 25 illustrates a resolution/goal interface 2500 in which a user may specify his or her goal for an upcoming occurrence or, in an exemplary embodiment, a goal for the upcoming year. For example, interface 2500 provides an entry field 2503 for specifying a number of miles the user wants to run in the next year. The user may also select other types of goals/resolutions by selecting any of options 2505 such as frequency, calories burned and speed. Once finalized, the user may then place the resolution or goal into effect using option 2507.

Figure 26:
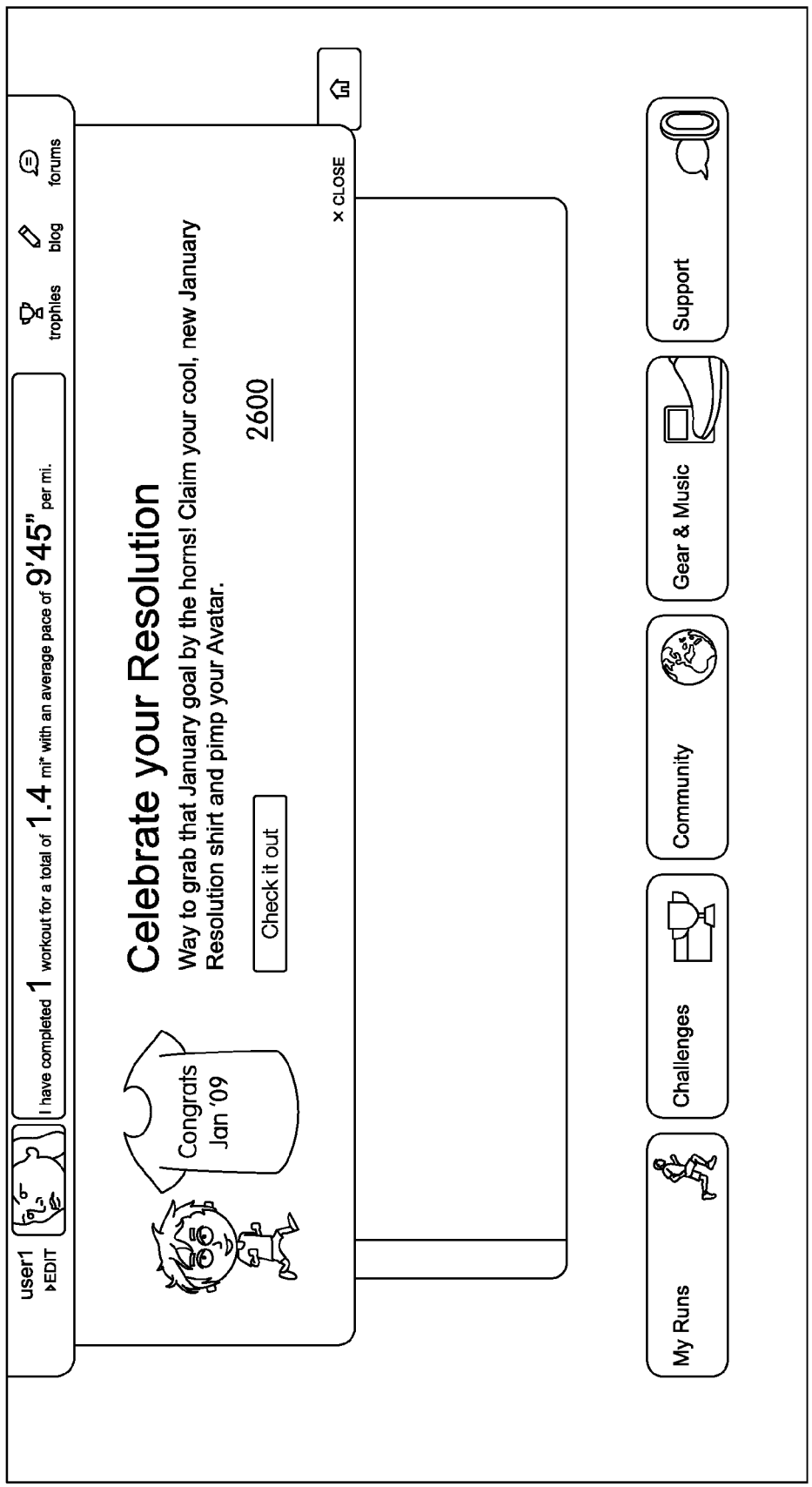
FIG. 26 illustrates an example award notification according to one or more aspects described herein.

As an incentive (or a further incentive) to complete the user's resolution, various awards or prizes may be unlocked upon completion of the user's resolution or a portion of the resolution. For example, a resolution or goal may be divided into mini-goals for each week, day, month, bi-week and the like. Upon completing the mini-goal, the user may be awarded with a prize. In one configuration, the prize or award may include an accessory (e.g., a shirt, shoes, pants, headband, other wearable items, new hairstyle, etc.) for the user's avatar. FIG. 26 illustrates a notification 2600 of a new award issued to a user upon completion of a January portion of his or her resolution/goal. The award may indicate the event. For example, a shirt awarded to a user for completion of the January mini-goal may include the words "Congrats Jan '09."

Figure 27:
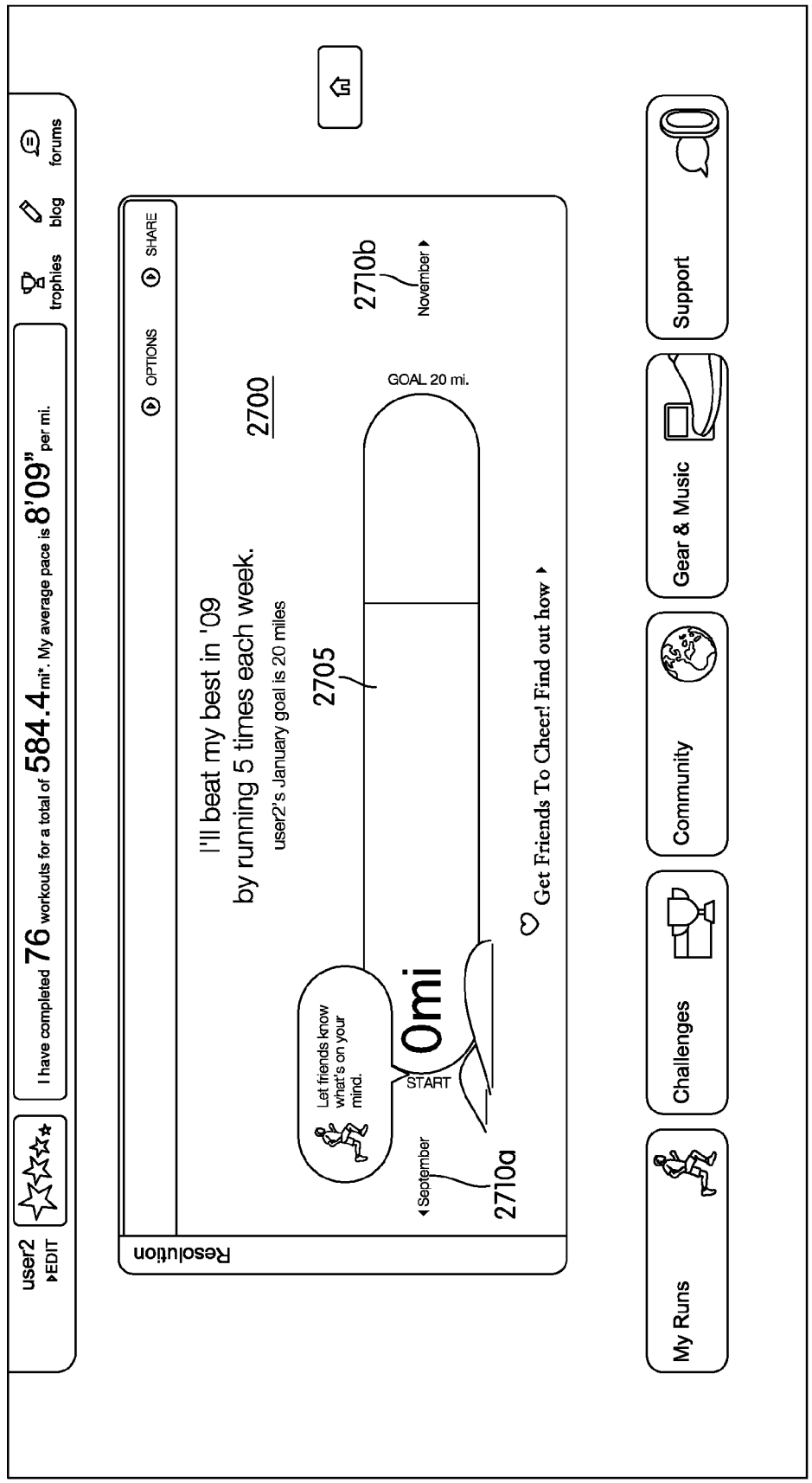
FIG. 27 illustrates an example progress tracking interface according to one or more aspects described herein.

FIG. 27 illustrates a goal tracker for a particular month. Goal tracker 2700 includes a progress bar 2705 that specifies how far a user is in reaching the goal. The goal tracker 2700 may be generated to track target levels on a monthly, weekly or daily basis based on an overall yearly goal or resolution. For example, if a user's goal is to run 240 miles in a year, monthly goals may be generated for running 20 miles per month. Progress bar 2705 may be filled in accordance with a level of progress. The goal tracker 2700 may further be shared with friends or other users. A user may move from monthly goal to monthly goal using options 2710*a* and *b*. Subgoals (e.g., monthly or weekly goals based on a yearly resolution) might not be divided evenly. For example, a running subgoal for January may be less than a subgoal for May based on weather forecasts.

A user may further brag or boast about certain accomplishments. A user may, for instance, display a message indicating a number of miles the user has run or distance the user has walked. The message may be displayed in terms of other items. For example, a user may brag about a number of calories burned by converting it into a number of hamburgers burned (i.e., based on an average calorie count of hamburgers). In another example, a user may boast about a distance run by posting a message showing a number of shoes worn through. Other variations may also be used.

Numerous specific details have been set forth herein to provide a thorough understanding of the embodiments. It will be understood by those skilled in the art, however, that the embodiments may be practiced without these specific details. In other instances, well-known operations and components have not been described in detail so as not to obscure the embodiments. It can be appreciated that the specific structural and functional details disclosed herein may be representative and do not necessarily limit the scope of the embodiments.

It is also worthy to note that any reference to "one embodiment" or "an embodiment" means that a particular feature, structure, or characteristic described in connection with the embodiment is included in at least one embodiment. The appearances of the phrase "in one embodiment" in various places in the specification are not necessarily all referring to the same embodiment.

Some embodiments may be implemented using an architecture that may vary in accordance with any number of factors, such as desired computational rate, power levels, heat tolerances, processing cycle budget, input data rates, output data rates, memory resources, data bus speeds and other performance constraints. For example, an embodiment may be implemented using software executed by a general-purpose or special-purpose processor. In another example, an embodiment may be implemented as dedicated hardware, such as a circuit, an application specific integrated circuit (ASIC), Programmable Logic Device (PLD) or digital signal processor (DSP), and so forth. In yet another example, an embodiment may be implemented by any combination of programmed general-purpose computer components and custom hardware components. The embodiments are not limited in this context.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, also may mean that two or more elements are not in direct contact with each other, but yet still co-operate or interact with each other. The embodiments are not limited in this context.

Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, such as the examples given with reference to FIG. 2. For example, the memory unit may include any memory device, memory article, memory medium, storage device, storage article, storage medium and/or storage unit, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, various types of Digital Versatile Disk (DVD), a tape, a cassette, or the like. The instructions may include any suitable type of code, such as source code, compiled code, interpreted code, executable code, static code, dynamic code, and the like. The instructions may be implemented using any suitable high-level, low-level, object-oriented, visual, compiled and/or interpreted programming language, such as C, C++, Java, BASIC, Perl, Matlab, Pascal, Visual BASIC, assembly language, machine code, and so forth. The embodiments are not limited in this context.

While certain features of the embodiments have been illustrated as described herein, many modifications, substitutions, changes and equivalents will now occur to those skilled in the art. It is therefore to be understood that the appended claims are intended to cover all such modifications and changes as fall within the true spirit of the embodiments.

What is claimed is:

1. A method comprising:
receiving, by an electronic avatar widget executing on a first network site, athletic performance information of a user from a second network site, wherein the electronic avatar widget includes portable code for displaying an avatar associated with the user on the first network site, wherein the first network site and the second network site each host a different website on which the avatar is displayed; and
modifying an appearance of the electronic avatar widget on the first network site in accordance with the athletic performance information received from the second network site, wherein the electronic avatar widget is configured to retrieve the athletic performance information and updates to an appearance of the avatar from the second network site.

2. The method of claim 1, wherein the avatar widget includes a display of athletic performance statistics of the user.

3. The method of claim 2, wherein modifying the appearance of the electronic avatar widget includes modifying the athletic performance statistics.

4. The method of claim 1, wherein modifying the appearance of the electronic avatar widget includes modifying the appearance of the avatar on the first network site based on the retrieved updates to the appearance of the avatar.

5. The method of claim 4, wherein modifying the appearance of the avatar includes modifying apparel worn by the avatar.

6. The method of claim 1, further comprising:
detecting that a privacy setting unique to at least one of the avatar and the user has been set to private on the second network site; and
in response, modifying the electronic avatar widget to hide athletic performance information within the electronic avatar widget executing on the first network site.

7. The method of claim 6, further comprising modifying the electronic avatar widget to hide the avatar in response to detecting that the avatar has been set to private.

8. The method of claim 1, wherein the electronic avatar widget includes an interactive option to create an avatar.

9. The method of claim 1, wherein the second network site includes a webpage.

10. The method of claim 1, wherein the electronic avatar widget includes dialogue of the avatar generated based on user-entered comments.

11. The method of claim 10, wherein the dialogue is user-modifiable.

12. A method comprising:
receiving an athletic performance goal of a first user for an upcoming time period, wherein the athletic performance goal includes a user-defined challenge involving a second user;
generating a display of an electronic avatar representing the second user on a first website;
receiving a user definition of an award for satisfying a specified condition of the athletic performance goal;
receiving, at the first website, athletic performance information of the second user from a second website, wherein the first website and the second website each host a different website on which the avatar is displayed;
determining that the second user has satisfied the specified condition in accordance with the received athletic performance information;
in response to determining that the second user has satisfied the specified condition:
providing the second user with the award, wherein the award is configured to modify an attribute of the electronic avatar representing the second user to be displayed on the first website, wherein the award includes a virtual piece of attire configured to be digitally wearable by the electronic avatar, wherein digitally wearing the virtual piece of attire by the electronic avatar includes modifying a visual attire of the electronic avatar; and
modifying the attribute of the electronic avatar displayed on the first website in accordance with the award,
wherein the first website is configured to retrieve the athletic performance information and the award from the second website.

13. The method of claim 12, wherein the award is provided by the first user.

14. The method of claim 12, wherein the award further includes a non-avatar related item.

15. The method of claim 14, wherein the non-avatar related item includes a gift card.

16. The method of claim 14, wherein the non-avatar related item includes apparel.

17. The method of claim 12, further comprising dividing the athletic performance goal into at least one subgoal corresponding to a period of time smaller than the upcoming time period.

18. The method of claim 17, wherein the specified condition corresponds to completion of the subgoal.

19. The method of claim 17, wherein the athletic performance goal is divided into a plurality of subgoals and wherein completion of each subgoal by the second user results in an award configured to modify an attribute of the electronic avatar.

20. The method of claim 19, wherein the upcoming period of time is a next year and wherein each of the plurality of subgoals corresponds to a different one of a plurality of months in the next year.

21. The method of claim 12, wherein the award is further configured to modify a hairstyle of the electronic avatar.

22. The method of claim 12, wherein the virtual piece of attire includes a style of shoe worn by the avatar.

23. The method of claim 12, wherein the virtual piece of attire includes a shirt worn by the avatar.

24. The method of claim 12, wherein the virtual piece of attire includes a virtual piece of sporting equipment associated with the avatar.

25. The method of claim 12, further comprising providing an option to set the athletic performance goal, wherein the option is configured to set the athletic performance goal to exceed an athletic performance statistic determined based on one or more past athletic performances.

26. The method of claim 12, further comprising receiving athletic performance data for the second user from an athletic performance monitoring device, wherein determining that the second user has satisfied the specified condition includes processing the received athletic performance data.

* * * * *